(12) United States Patent
Snow

(10) Patent No.: US 11,491,201 B2
(45) Date of Patent: Nov. 8, 2022

(54) COMPOSITIONS AND METHODS FOR THE TREATMENT OF "PLAQUES AND TANGLES" IN HUMANS AND ANIMALS

(71) Applicant: COGNITIVE CLARITY INC., Edmonds, WA (US)

(72) Inventor: Alan Snow, Edmonds, WA (US)

(73) Assignee: Cognitive Clarity Inc., Edmonds, WA (US)

( * ) Notice: Subject to any disclaimer, the term of this patent is extended or adjusted under 35 U.S.C. 154(b) by 0 days.

(21) Appl. No.: 16/697,171

(22) Filed: Nov. 26, 2019

(65) Prior Publication Data

US 2020/0188467 A1  Jun. 18, 2020

Related U.S. Application Data

(60) Provisional application No. 62/778,875, filed on Dec. 12, 2018.

(51) Int. Cl.
| | | |
|---|---|---|
| *A61K 36/00* | (2006.01) | |
| *A61K 36/82* | (2006.01) | |
| *A61K 36/185* | (2006.01) | |
| *A61P 25/28* | (2006.01) | |
| *A61K 9/48* | (2006.01) | |
| *A61K 9/00* | (2006.01) | |
| *A61K 36/74* | (2006.01) | |

(52) U.S. Cl.
CPC ............ *A61K 36/82* (2013.01); *A61K 9/0095* (2013.01); *A61K 9/48* (2013.01); *A61K 36/185* (2013.01); *A61K 36/74* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 5,683,698 A * | 11/1997 | Chavali | A61K 36/59 424/756 |
| 6,264,994 B1 | 7/2001 | Castillo et al. | |
| 6,346,280 B1 | 2/2002 | Castillo et al. | |
| 6,939,570 B1 | 9/2005 | Snow et al. | |
| 7,148,001 B2 | 12/2006 | Castillo et al. | |
| 10,307,745 B2 | 6/2019 | Albert et al. | |
| 10,350,258 B2 | 7/2019 | Cam et al. | |
| 2001/0055630 A1 | 12/2001 | Castillo et al. | |
| 2007/0190075 A1 | 8/2007 | Suzuki et al. | |
| 2012/0053138 A1 | 3/2012 | Jia et al. | |
| 2015/0017108 A1 | 1/2015 | Wang | |
| 2016/0250273 A1 | 9/2016 | Cam et al. | |
| 2019/0350996 A1 | 11/2019 | Cam et al. | |

FOREIGN PATENT DOCUMENTS

| | | |
|---|---|---|
| CN | 01712640 | 5/2010 |
| EP | 3 261 655 | 1/2018 |
| JP | 2003-171298 A | 6/2003 |
| JP | 2005-298425 A | 10/2005 |
| JP | 2007-182403 A | 7/2007 |
| JP | 2007-230977 A | 9/2007 |
| JP | 2007-277163 | 10/2007 |
| JP | 2010-013423 | 1/2010 |
| JP | 2013-169153 | * 9/2013 |
| WO | WO-98/51302 | 11/1998 |
| WO | WO-00/30666 A1 | 6/2000 |
| WO | WO-00/33659 A1 | 6/2000 |
| WO | WO-2016/138270 A3 | 9/2016 |

OTHER PUBLICATIONS

Amen, "12 prescriptions for creating a brain healthy life." Retrieved Jun. 23, 2016, from: www.amenclinics.com/cybcyb/12-prescriptions-for-creating-a-brain-healthy-life.
Arai et al., "Argyrophilic glial inclusions in the midbrain of patients with Parkinson's disease and diffuse Lewy body disease are immunopositive for NACP/.alpha.-synuclein." Neurosc. Lett. 259: 83-86 (1999).
Askanas et al., Ann. Neurol. 43: 521-560, 1993.
Barghorn et al., "Purification of Recombinant Tau Protein and Preparation of Alzheimer-Paired Helical Filaments In Vitro," Methods Mol. Biol. 299: 35-51 (2005).
Breslow, "New: 87 deceased NFL players test positive for brain disease." Frontline, Jan. 9, 2016. Retrieved Jun. 23, 2016, from http://www.pbs.org/wgbh/frontline/article/new-87-deceased-nfl-players-test-positive-for-brain-disease/.
Capucchio et al., "Parenchymal and vascular lesions in ageing equine brains: histological and immunohistochemical studies." J. Comp. Pathol. 142(1): 61-73 (2010).
Chen et al., "A learning deficit related to age and .beta.-amyloid plaques in a mouse model of Alzheimer's disease." Nature 408: 975-979 (2000).
Dotinga, R., Plaques, Tangles in Brain Don't Always Lead to Alzheimer's, https:/www.medicinenet.com/script/main/art.asp?articlekey?100750, dated May 27, 2009, (accessed Jan. 7, 2019).
Dumont et al., "Bezafibrate administration improves behavioral deficits and tau pathology in P3015 mice," Human Molecular Genetics 21: 5091-5105 (2012).
Elder, et al., Transgenic Mouse Models of Alzheimer's Disease, 77(1):69-81 (2010).
Flood et al., "Amnestic effects in mice of four synthetic peptides homologous to amyloid .beta. protein from patients with Alzheimer disease," Proc. Natl. Acad. Sci. USA 88(8): 3363-3366 (1991).

(Continued)

*Primary Examiner* — Michael V Meller
(74) *Attorney, Agent, or Firm* — Foley & Lardner LLP

(57) ABSTRACT

Composition and methods for treating brain "plaques" and/or "tangles" in a subject wherein the method comprises administration of a therapeutically effective amount of a composition comprising a black currant extract, *Uncaria tomentosa* extract, and an oolong tea extract.

10 Claims, 24 Drawing Sheets
(16 of 24 Drawing Sheet(s) Filed in Color)

(56) References Cited

OTHER PUBLICATIONS

Flood et al., "An amyloid β-protein fragment, Aβ[12-28], equipotently impairs post-training memory processing when injected into different limbic system structures." Brain Res. 663(2): 271-276 (1994).
Friedhoff et al., "Rapid Assembly of Alzheimer-like Paired Helical Filaments from Microtubule-Associated Protein Tau Monitored by Fluorescence in Solution," Biochemistry 37(28): 10223-10230 (1998).
Games et al., "Alzheimer-type neuropathology in transgenic mice overexpressing V717F .beta.-amyloid precursor protein," Nature 373: 523-527(1995).
Giannakopoulos et al., "Tangle and neuron numbers but not amyloid load, predict cognitive status in Alzheimer's disease." Neurology 60(9): 1495-1500 (2003).
Glenner and Wong, "Alzheimer's disease: initial report of the purification and characterization of a novel cerebrovascular amyloid protein." Biochem. Biophys. Res. Comm. 120(3): 885-890 (1984).
Grundke-Iqbal et al., "Abnormal phosphorylation of microtubule-associated protein T (tau) in Alzheimer cytoskeletal pathology," Proc. Natl. Acad. Sci. USA 83(13): 4913-4917 (1986).
Gunn-Moore et al., "Cognitive dysfunction and the neurobiology of ageing in cats." J Small Anim. Pract. 48: 546-553 (2007).
Haass et al., "The Swedish mutation causes early-onset Alzheimer's disease by bold beta-secretase cleavage within the secretory pathway." Nature Med. 1: 1291-1296 (1995).
Hardy, "Framing beta-amyloid." Nature Genet. 1: 223-234 (1992).
Harrigan et al., "Beta amyloid is neurotoxic in hippocampal slice cultures," Neurobiol. Aging 16: 779-789 (1995).
Hsiao et al., "Correlative memory deficits, Abeta elevation, and amyloid plaques in transgenic mice." Science 274(5284): 99-102 (1996).
International Preliminary Report on Patentability (Chapter 1) for Application No. PCT/US2016/019572, dated Sep. 8, 2017. (9 pages).
International Search Report and Written Opinion for PCT/US2019/063455 dated Mar. 17, 2020, 15 pages.
International Search Report and Written Opinion on PCT/US2016/019572, dated Aug. 29, 2016.
International Search Report and Written Opinion received in Singapore Application No. 11201706861Q dated Jul. 30, 2018.
Janus et al., "A .beta, peptide immunization reduces behavioral impairment and plaques in a model of Alzheimer's disease." Nature 408: 979-982 (2000).
Karlnoski et al., "Suppression of amyloid deposition leads to long-term reductions in Alzheimer's pathologies in Tg2576 mice." J. Neurosc. 29(15): 4964-4971 (2009).
Kosik et al., "Microtubule-associated protein tau (tau) is a major antigenic component of paired helical filaments in Alzheimer disease." Proc. Natl. Acad. Sci. USA 83(11): 4044-4048 (1986).
Lee et al., "A68: a major subunit of paired helical filaments and derivatized forms of normal Tau." Science 251(4994): 675-678 (1991).
Lee et al., "Neurodegenerative tauopathies." Ann. Rev. Neurosci. 24: 1121-1159 (2001).
Levine, "Thioflavine T interaction with amyloid β-sheet structures," Amyloid 2(1): 1-6 (1995).
Levine, "Thioflavine T interaction with synthetic Alzheimer's disease beta-amyloid peptides: detection of amyloid aggregation in solution." Protein Sci. 2(3): 404-410 (1993).
Mandybur, J. "Cerebral amyloid angiopathy: the vascular pathology and complications." Neuropath. Exp. Neurol. 45(1): 79-90 (1986).
Masters et al., "Amyloid plaque core protein in Alzneimer disease and Down syndrome." Proc. Natl. Acad. Sci. USA 82(12): 4245-4249 (1985).
Morgan et al., "A .beta, peptide vaccination prevents memory loss in an animal model of Alzheimer's disease." Nature 408(6815): 982-985 (2000).
Murrell et al., "A mutation in the amyloid precursor protein associated with hereditary Alzheimer's disease." Science 254(5028): 97-99 (1991).

Naiki and Nakakuki, "First-order kinetic model of Alzheimer's beta-amyloid fibril extension in vitro." Lab. Invest. 74(2): 374-383 (1996).
Nakai et al., "Kinetic analysis of amyloid fibril polymerization in vitro." Lab Invest. 65(1): 104-110 (1991).
Nakamura et al., "Histopathological studies of senile plaques and cerebral amyloidosis in cynomolgus monkeys." J. Med. Primatol. 27(5): 244-252 (1998).
Nakamura et al., "Senile plaques in an aged two-humped (Bactrian) camel (*Camelus bactrianus*)." Acta Neuropath. 90(4): 415-418 (1995).
Nakamura et al., "Senile plaques in very aged cats." Acta Neuropath. 91: 437-439 (1996).
Ng, et al. Tea consumption and cognitive impairment and decline in older Chinese adults, Am J. Clin Nutr 2008; 88:224-31.
Oddo et al., "Reduction of soluble Abeta and tau, but not soluble Abeta alone, ameliorates cognitive decline in transgenic mice with plaques and tangles." J. Biol. Chem. 281(51): 39413-39423 (2006).
Omalu et al., "Emerging histomorphologic phenotypes of chronic traumatic encephalopathy in American athletes." Neurosurgery 69(1): 173-183 (2011).
Papaioannou et al., "Immunohistochemical investigation of the brain of aged dogs. I. Detection of neurofibrillary tangles and of 4-hydroxynoneal protein, an oxidating damage product, in senile plaques." Amyloid 8(1): 11-21 (2001).
Pardridge et al., "Amyloid Angiopathy of Alzheimer's Disease: Amino Acid Composition and Partial Sequence of a 4,200-Dalton Peptide Isolated from Cortical Microvessels," J. Neurochem. 49(5): 1394-1401 (1987).
Pike et al., "In vitro aging of .beta.-amyloid protein causes peptide aggregation and neurotoxicity." Brain Res. 563(1-2): 311-314 (1991).
Pike et al., "Structure-Activity Analyses of .beta.-Amyloid Peptides: Contributions of the .beta.25-35 Region to Aggregation and Neurotoxicity," J. Neurochem. 64: 253-265 (1995).
Pollanen et al., "Pathology and biology of the Lewy body," J. Neuropath. Exp. Neurol. 52(3): 183-191 (1993).
Rajput et al., "Parkinsonism, Lrrk2/G2019S, and tau neuropathology," Neurology 67(8): 1506-1508 (2006).
Sandoval et al., "Anti-inflammatory and antioxidant activities of cat's claw (Uncaria tomentosa and Uncaria guianensis) are independent of their alkaloid content," Phytomedicine, 2002, vol. 9, No. 4, pp. 325-337.
Santacruz et al., "Tau suppression in a neurodegenerative mousel model improves memory function." NIH-PA Author Manuscript (2006), also published in Science 309(5733): 476-481 (2005).
Santpere and Ferrer, :LRRK2 and neurodegeneration. Acta Neuropathol. 117: 227-246 (2009).
Schenk et al., "Immunization with amyloid-.beta. attenuates Alzheimer-disease like pathology in PDAPP mouse." Nature 400: 173-177 (1999).
Siegel, G. et al., Abstract P356: In vitro effect of blackcurrant anthocyanins on flow-dependent dilatation of human intracerebral arteries and Alzheimer nanoplaque formation, Circulation, 2012, vol. 125, Abstract P356 abstract.
Spillantini et al., ".alpha.-Synuclein in filamentous inclusions of Lewy bodies from Parkinson's disease and dementia with Lewy bodies." Proc. Natl. Acad. Sci. USA 95(11): 6469-6473 (1998).
Stern, Y., Cognitive reserve in ageing and Alzheimer's disease, Lancet Neurol., 11(11):1006-1012 (2012).
Takeda, et al., Senescence-accelerated mouse (SAM): a novel murine model of senescence, 32(1-2):105-9 (1997)(Abstract Only).
Tanzi et al., "Protease inhibitor domain encoded by an amyloid protein precursor mRNA associated with Alzheimer's disease," Nature 331: 528-530 (1988).
Uchida et al., "Amyloid angiopathy with cerebral hermorrhage and senile plaque in aged dogs." Jpn. J. Vet. Sci. 52(3): 605-611 (1990).
Uchida et al., "Senile plaques and other senile changes in the brain of an aged American black bear," Vet. Pathol. 32(4): 412-414 (1995).
Van Broeckhoven et al., "Amyloid beta protein precursor gene and hereditary cerebral hemorrhage with amyloidosis (Dutch)." Science 248(4959): 1120-1122 (1990).

(56) References Cited

OTHER PUBLICATIONS

Vellas et al., "Long-term follow-up of patients immunized with AN1792: Reduced functional decline in antibody responders." Current Alz. Res. 6(2): 144-152 (2009).
Vepsalainen, S. et al., "Anthocyanin-enriched bilberry and blackcurrant extracts modulate amyloid precursor protein processing and alleviate behavioral abnormalities in the APP/PSI mouse model of Alzheimer's disease," Journal of Nutritional Biochemistry, 2013, vol. 24, pp. 360-370 abstract; and p. 361.
Wakabayashi et al., "Accumulation of α-synuclein/NACP is a cytopathological feature common to Lewy body disease and multiple system atrophy." Acta Neuropath. 96(5): 445-452 (1998).
WHO-IUIS Nomenclature Sup-Committee, "Nomenclature of amyloid and amyloidosis." Bull. WHO 71: 105-108 (1993).
Yamakawa, M.Y. et al., "Anthocyanin suppresses the toxicity of Aβ deposits through diversion of molecular forms in in vitro and in in vivo models of Alzheimer's disease," Nutritional Neuroscience, 2016, vol. 19, No. 1, pp. 32-42.
Yanamandra et al., Anti-tau antibodies that block tau aggregate seeding in vitro markedly decreases pathology and improves cognition in vivo. Neuron 80(2): 402-414 (2013).
Zhang Yufang et al., "Progress on interaction and production of amyloid-β and tau protein during Alzheimer disease," Chinese Journal of Geratrics, 32:1 pp. 105, Jan. 31, 2013 English Translation (Google).
Chinese Search Report on CN 201680019588.2 dated Jan. 26, 2021 (English translation).
Ghosh et al. "Cytoprotective Effects of Anthocyanins and Other Phenolic Fractions of Boysenberry and Blackcurrant on Dopamine and Amyloid B-induced oxidativeStress in Transfected COS-7 Cells," Sci Food Agric (87):2061-2067 (2007).

* cited by examiner

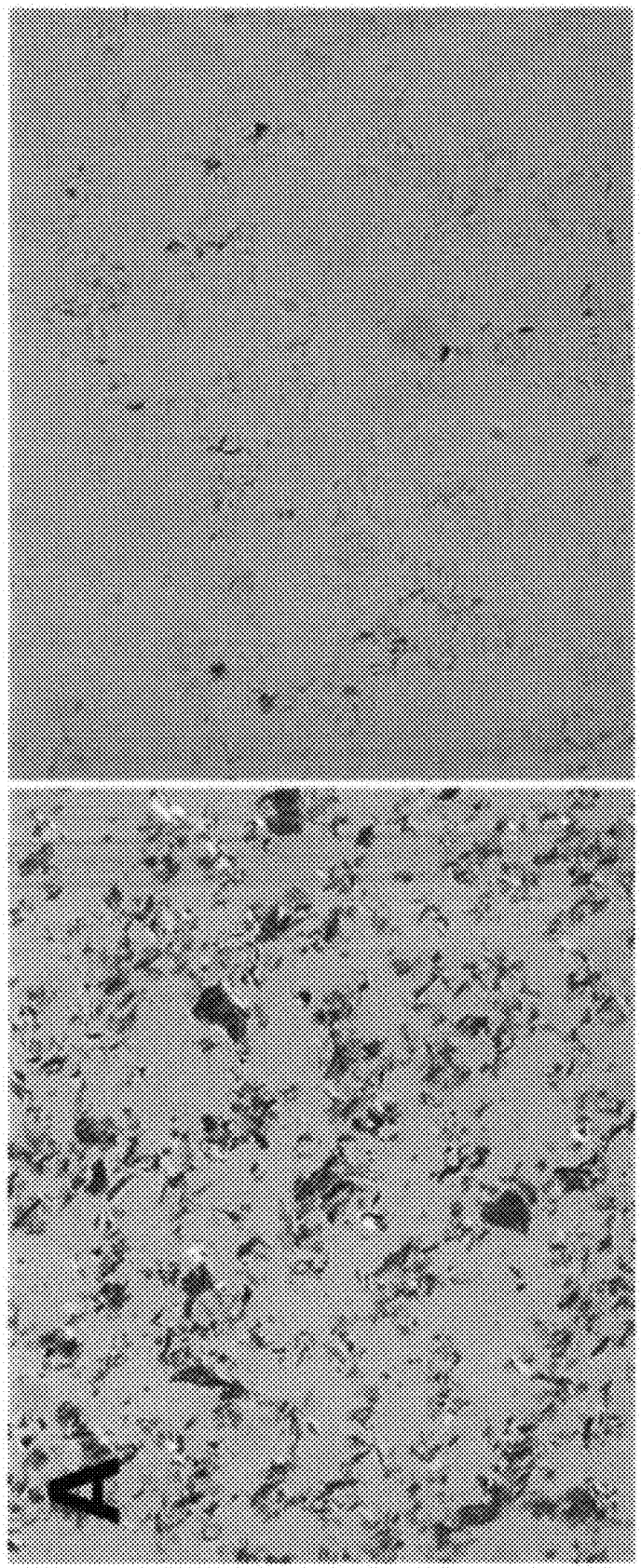

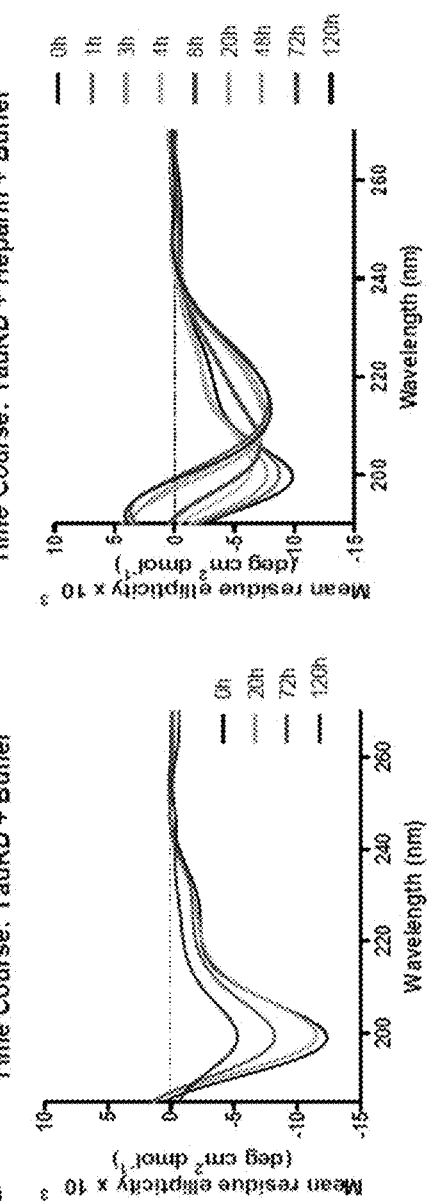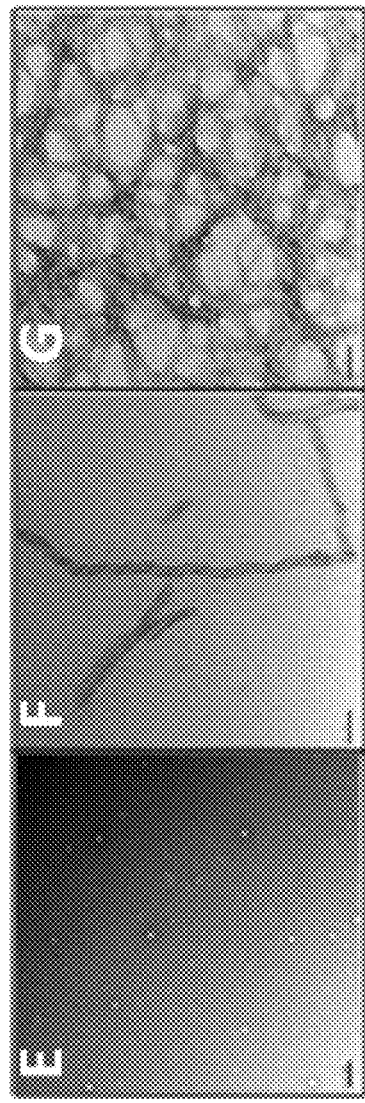
FIG. 5A FIG. 5B FIG. 5C
FIG. 5D FIG. 5E FIG. 5F FIG. 5G

COMPOSITIONS AND METHODS FOR THE TREATMENT OF "PLAQUES AND TANGLES" IN HUMANS AND ANIMALS

RELATED APPLICATIONS

This application claims the priority benefits of U.S. provisional application 62/778,875 filed Dec. 12, 2018, the entire contents of which are incorporated herein by reference.

TECHNICAL FIELD

The invention relates to blended compositions of plant extracts of black currant, *Uncaria tomentosa*, and oolong tea and methods of using such compositions for treating "plaques" and "tangles" that accumulate in the aging brain in amyloidosis and tauopathies in humans and animals (e.g., such as aged dogs and cats). In addition, the invention relates to the development of a nutraceutical blended composition consisting of a combination of a black currant extract, a plant extract of *Uncaria tomentosa*, and an oolong tea extract, to prevent and treat traumatic brain injury (TBI), concussions (as observed in most athletes and the military/soldiers), single and repeated blows to the head, and chronic traumatic encephalopathy (CTE). Lastly, this invention relates to the surprising discovery that the blended compositions are more soluble than blended compositions containing *Uncaria tomentosa* and oolong tea and no black currant extract.

BACKGROUND OF THE INVENTION

Amyloidosis and the Accumulation of Beta-Amyloid Plaques in the Brain of a Variety of Disorders Alzheimer's disease is characterized by the accumulation of a 39-43 amino acid peptide termed the beta-amyloid protein or Aβ, in a fibrillary form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, a characteristic hallmark of Alzheimer's disease. Accumulating evidence implicates amyloid, and more specifically, the formation, deposition, accumulation and/or persistence of Aβ fibrils, as a major causative factor of Alzheimer's disease pathogenesis. In addition, besides Alzheimer's disease, a number of other amyloid diseases involve formation, deposition, accumulation and persistence of Aβ fibrils, including Down's syndrome, disorders involving congophilic angiopathy, such as but not limited to, hereditary cerebral hemorrhage of the Dutch type, inclusion body myositosis, dementia pugilistica, cerebral β-amyloid angiopathy, dementia associated with progressive supranuclear palsy, dementia associated with cortical basal degeneration and mild cognitive impairment.

The amyloid diseases (amyloidosis) are classified according to the type of amyloid protein as well as the underlying disease. Amyloid diseases have a number of common characteristics including each amyloid consisting of a unique type of amyloid protein. The amyloid diseases include, but are not limited to, the amyloid associated with Alzheimer's disease, Down's syndrome, Canine Dysfunction syndrome (CDS), Canine Cognitive Dysfunction (CCD), as seen in aged animals such as dogs and cats, hereditary cerebral hemorrhage with amyloidosis of the Dutch type, dementia pugilistica, inclusion body myositosis (Askanas et al., Ann. Neurol. 43:521-560, 1993) and mild cognitive impairment (where the specific amyloid is referred to as beta-amyloid protein or Aβ), the amyloid associated with chronic inflammation, various forms of malignancy and Familial Mediterranean Fever (where the specific amyloid is referred to as AA amyloid or inflammation-associated amyloidosis), the amyloid associated with multiple myeloma and other B-cell dyscrasias (where the specific amyloid is referred to as AL amyloid), the amyloid associated with type 2 diabetes (where the specific amyloid is referred to as amylin or islet amyloid polypeptide or IAPP), the amyloid associated with the prion diseases including Creutzfeldt-Jakob disease, Gerstmann-Straussler syndrome, kuru and animal scrapie (where the specific amyloid is referred to as PrP amyloid), the amyloid associated with long-term hemodialysis and carpal tunnel syndrome (where the specific amyloid is referred to as α2-microglobulin amyloid), the amyloid associated with senile cardiac amyloidosis and Familial Amyloidotic Polyneuropathy (where the specific amyloid is referred to as transthyretin or prealbumin), and the amyloid associated with endocrine tumors such as medullary carcinoma of the thyroid (where the specific amyloid is referred to as variants of procalcitonin). In addition, the α-synuclein protein which forms amyloid-like fibrils, and is Congo red and Thioflavin S positive (specific stains used to detect amyloid fibrillary deposits), is found as part of Lewy bodies in the brains of patients with Parkinson's disease, Lewy body disease (Lewy in Handbuch der Neurologie, M. Lewandowski, ed., Springer, Berlin pp. 920-933, 1912; Pollanen et al, *J. Neuropath. Exp. Neurol.* 52:183-191, 1993; Spillantini et al, *Proc. Natl. Acad. Sci. USA* 95:6469-6473, 1998; Arai et al, *Neurosc. Lett.* 259:83-86, 1999), multiple system atrophy (Wakabayashi et al, *Acta Neuropath.* 96:445-452, 1998), dementia with Lewy bodies, and the Lewy body variant of Alzheimer's disease. For purposes of this disclosure, Parkinson's disease, due to the fact that fibrils develop in the brains of patients with this disease (which are Congo red and Thioflavin S positive, and which contain predominant beta-pleated sheet secondary structure), is now regarded as a disease that also displays the characteristics of an amyloid-disease.

Amyloid as a Therapeutic Target for Alzheimer's Disease

Alzheimer's disease is characterized by the deposition and accumulation of a 39-43 amino acid peptide termed the beta-amyloid protein, Aβ or β/A4 (Glenner and Wong, *Biochem. Biophys. Res. Comm.* 120:885-890, 1984; Masters et al, *Proc. Natl. Acad. Sci. USA* 82:4245-4249, 1985; Husby et al, Bull. *WHO* 71:105-108, 1993). Aβ is derived by protease cleavage from larger precursor proteins termed β-amyloid precursor proteins (APPs) of which there are several alternatively spliced variants. The most abundant forms of the APPs include proteins consisting of 696, 751 and 770 amino acids (Tanzi et al, *Nature* 31:528-530, 1980.

The small Aβ peptide is a major component that makes up the amyloid deposits or "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al, *Proc. Natl. Acad. Sci. USA* 83:4913-4917, 1986; Kosik et al, *Proc. Natl. Acad. Sci. USA* 83:4044-4048, 1986; Lee et al, *Science* 251:675-678, 1991). The pathological hallmark of Alzheimer's disease is therefore the presence of both "plaques" and "tangles", with amyloid being deposited in the central core of the plaques. The other major type of lesion found in the Alzheimer's disease brain is the accumulation of amyloid in the walls of blood vessels, both within the brain parenchyma and in the walls of meningeal vessels that lie outside the brain. The amyloid deposits localized to the walls of blood vessels are referred to as cerebrovascular amyloid or congophilic angiopathy (Mandybur, *J. Neuropath. Exp. Neurol.* 45:79-90, 1986; Pardridge et al., *J. Neurochem.* 49:1394-1401, 1987).

For many years there has been an ongoing scientific debate as to the importance of "amyloid" in Alzheimer's disease, and whether the "plaques" and "tangles" characteristic of this disease were a cause or merely a consequence of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time (Pike et al, Br. Res. 563:311-314, 1991; *J. Neurochem.* 64:253-265, 1995). Studies show that it is the fibrillary structure (consisting of a predominant β-pleated sheet secondary structure) characteristic of all amyloids that is responsible for the neurotoxic effects. Aβ has also been found to be neurotoxic in slice cultures of hippocampus (Harrigan et al, *Neurobiol. Aging* 16:779-789, 1995) and to induce nerve cell death in transgenic mice (Games et al, *Nature* 373:523-527, 1995; Hsiao et al, Science 272:99-102, 1996). Injection of the Alzheimer's Aβ into rat brain also causes memory impairment and neuronal dysfunction (Flood et al, *Proc. Natl. Acad. Sci. USA* 88:3363-3366, 1991; Flood et al, Br. Res. 663:271-276, 1994).

Probably, the most convincing evidence that Aβ amyloid is directly involved in the pathogenesis of Alzheimer's disease comes from genetic studies. It was discovered that the production of Aβ can result from mutations in the gene encoding its precursor, β-amyloid precursor protein (Van Broeckhoven et al, *Science* 248:1120-1122, 1990; Murrell et al, Science 254:97-99, 1991; Haass et al, *Nature Med* 1: 1291-1296, 1995). The identification of mutations in the beta-amyloid precursor protein gene that cause early onset familial Alzheimer's disease is the strongest argument that amyloid is central to the pathogenic process underlying this disease. Several reported disease-causing mutations have been discovered which demonstrate the importance of Aβ in causing familial Alzheimer's disease (reviewed in Hardy, *Nature Genet.* 1:223-234, 1992). All of these studies suggest that providing a therapy, drug or supplement to reduce, eliminate and/or prevent fibrillary Aβ formation, deposition, accumulation and/or persistence in the brains of humans and animals, well serve as an effective therapeutic.

The Accumulation of "Plaques and Tangles" in the Aging Human and Animal Brain

The human brain is the most complex organ in the universe. It weighs only 3 pounds, or about 2% of body weight. Yet it uses 20-30% of the calories consumed, 20% of the oxygen breathed, and 25% of the blood flow in the body; it consists of 85% water (Daniel G. Amen, M. D. 12 prescriptions for creating a brain healthy life. Source: www.amenclinics.com/cybcyb/12-prescriptions-for-creating-a-brain-healthy-life/). There are approximately 100 billion nerve cells (i.e. neurons) in the brain, and up to a quadrillion connections called synapses (ibid). The human brain as it ages, loses about 85,000 cortical neurons per day, or about one every second (Deepak Chopra, M. D. and Rudolph Tanzi, Ph. D. Super Brain. Unleashing the Explosive Power of Your Mind to Maximize Health, Happiness, and Spiritual Well Being. See //www.chopra.com/superbrain-by-deepak-chopra-rudolph-tanzi.) As the brain ages, starting in the 20's, there is a slow but deliberate accumulation of two neurotoxic proteins. The first is the brain accumulation of an insoluble (aggregated) specific neurotoxic protein known as the "beta-amyloid protein" or Aβ. Beta-amyloid protein deposits in the form of "plaques" (looking like "meatballs" in the brain under a microscope), have been shown to be instrumental in killing healthy neurons that lead to a decline in hippocampus-dependent memory and cognition. Dr. Alan Snow and co-inventors developed patented methods to produce "plaques in a testtube" (identical to what is seen in the human brain) and used these methods to screen for and identify natural "plaquereducing" nutraceutical ingredients (U.S. Pat. No. 7,148, 001, which is incorporated herein by reference in its entirety).

The second neurotoxic protein that accumulates in the aging brain is known as the "tau protein" and forms twisted paired helical filaments known as "tangles." Neurofibrillary tangles accumulate inside neurons that causes them to die and look like "dried spaghetti strands" under a microscope. Dr. Snow's laboratories developed proprietary methods to form "tangles" in a test-tube, and then used these assays to identify "tangle-inhibiting" nutraceutical ingredients (see examples below). Thus, in the aging brain, both "plaques and tangles" accumulate, causing neurons to die; connections between nerve cells (called synapses) to disintegrate; and memory and cognition to progressively decline. Compounds or agents able to disaggregate and reduce the accumulation of "plaques and tangles" have been shown to lead to memory improvement and a reduction in memory decline (Karinoski et al. Suppression of amyloid deposition leads to long-term reductions in Alzheimer's pathologies in Tg2576 mice. *J. Neurosc.* 29:4964-4971, 2009; Vellas et al. Longterm follow-up of patients immunized with AN1792: Reduced functional decline in antibody responders. *Current Alz. Res.* 6:144-151, 2009; Morgan et al. Aβ peptide vaccination prevents memory loss in an animal model of Alzheimer's disease. *Nature* 408:982-985, 2000; Chen et al. A learning deficit related to age and β-amyloid plaques in a mouse model of Alzheimer's disease. *Nature* 408:975-979, 2000; Janus et al. Aβ peptide immunization reduces behavioral impairment and plaques in a model of Alzheimer's disease. *Nature* 408:979-985, 2000; Schenk et al. Immunization with amyloid-β attenuates Alzheimer-disease like pathology in PDAPP mouse. *Nature* 400:173-177, 1999; Yanamandra et al. Anti-tau antibodies that block tau aggregate seeding in vitro markedly decreases pathology and improves cognition in vivo. Neuron 80:402-414, 2013; Dumont et al. Bezafibrate administration improves behavioral deficits and tau pathology in P3015 mice. *Human Molecular Genetics* 21:5091-5105, 2012; Oddo et al. Reduction of soluble Abeta and tau, but not soluble Abeta alone, ameliorates cognitive decline in transgenic mice with plaques and tangles. *J. Biol. Chem.* 281:39413-39423, 2006; Santacruz et al. Tau suppression in a neurodegenerative mouse model improves memory function. *Science* 309:476-481, 2005.)

The only difference between an aging brain that could lead to age-associated memory impairment (AAMI), then to mild-cognitive impairment (MCI), and potentially to Alzheimer's disease, and a brain that does not, is the number of "plaques and tangles" in the brain. Alzheimer's disease brains are loaded with tens to hundreds of thousands of "plaques and tangles," per square millimeter, causing a marked increase in the death of neurons, leading to a loss of synapses (connections between neurons), and concurrent memory loss and cognitive decline.

Therefore, beta-amyloid and tau are two key proteins in the aging brain that accumulate as insoluble "plaques and tangles" that have been shown to be directly linked to memory loss and cognitive decline. There is currently no pharmaceutical drug that has been approved for reducing and removing both beta-amyloid protein "plaques" and tau protein-containing "tangles" in the brain.

The Accumulation of "Plaques" in the Aging Dog and Cat Brain

Dogs and cats also accumulate "plaques" (and, to a lesser extent, "tangles") in their brains as they age that are believed to contribute to memory decline and cognitive impairment. The same beta-amyloid protein (i.e. "plaques") and tau protein ("tangles") that accumulate in the human brain also accumulate in aged dogs (Papoiannou et al, Immunohistochemical investigation of the brain of aged dogs. I. Detection of neurofibrillary tangles and of 4-hydroxynonenal protein, an oxidative damage product, in senile plaques. *Amyloid* 8:11-21, 2001; Uchida et al, Amyloid angiopathy with cerebral hemorrhage and senile plaque in aged dogs. *Nihon Juigaku Zasshi* 52: 605-11, 1990) and cats (Gunn-Moore et al, Cognitive dysfunction and the neurobiology of ageing in cats. *J Small Anim. Pract.* 48: 546-53, 2007; Nakamura et al. Senile plaques in very aged cats. *Acta Neuropath.* 91: 437-9, 1996).

Canine Cognitive Dysfunction (CCD) (also known as Cognitive Dysfunction Syndrome or CDS) is a disease prevalent in dogs (and cats) that exhibit symptoms of dementia or Alzheimer's disease as seen in humans. CCD creates pathological changes in the brain that slow the mental functioning of dogs (and cats) resulting in loss of memory, motor function and learned behaviors from training early in life. In the dog's and cat's brain, the culprit is again the beta-amyloid protein or Aβ that forms "plaques" in the brain. As the dog ages, more and more "plaques" accumulate and nerve cells die. Although the initial symptoms of the disorders are mild, they gradually worsen over time, also known as "cognitive decline". Amyloid "plaques" occur in aged dogs at about five to seven years of age, and in cats of about ten years of age (which is proportional to their average lifespan of 15-20 years). In fact, clinical signs of cognitive dysfunction syndrome are found in 50% of dogs over the age of 11, and by the age of 15, 68% of dogs display at least one sign. Dogs will often find themselves confused in familiar places of the home, spending long periods of time in one area of the home, not responding to calls or commands, and experiencing abnormal sleeping patterns.

Beta-amyloid protein containing "plaques" also have been identified in the brains of other higher mammals including monkeys, bears, camels, and horses. (Nakamura et al, Histopathological studies of senile plaques and cerebral amyloidosis in cynomolgus monkeys. *J Med Primatol.* 27: 244-52, 1998; Capucchio et al. studies. *J Comp Pathol* 142: 61-73, 2010; Nakamura et al, Senile plaques in an aged two-humped (Bactrian) camel (*Camelus bactrianus*), *Acta Neuropathol* 90: 415-8, 1995; Uchida et al, Senile plaques and other senile changes in the brain of an aged American black bear, *Vet. Pathol.* 32: 412-4, 1995).

Tauopathies and "Tangles"

Tau was discovered in the mid-1970s as a microtubule associated protein (Weingarten, 1975). Besides being a stabilizer of microtubules in neurons and other cells, it has since been found to play important roles in cell differentiation, polarization and axonal transport. Normal tau is a soluble protein bound to microtubules, but in a series of neurodegenerative diseases, now known as tauopathies, tau accumulates as a pathogenic insoluble, fibrillar protein. These tau inclusions appear to modulate the severity of dementia and clinical features of these neurodegenerative diseases. Tauopathies include diseases such as Alzheimer's disease, frontotemporal lobar degeneration with tau inclusions (FTLD-tau) such as Pick's disease, progressive supranuclear palsy, and corticobasal degeneration, agyrophillic grain disease, some prion diseases, amyotrophic lateral sclerosis/parkinsonism-dementia complex, chronic traumatic encephalopathy, and some genetic forms of Parkinson's disease (V. M. Lee et al., *Ann. Rev. Neurosci.* 24: 1121-1159, 2001; B. Omalu et al., *Neurosurgery* 69(1):173-83, 2011; A. Rajput et al., *Neurology* 67: 1506-1508, 2006; G. Santpere and I. Ferrer, *Acta Neuropathol.* 117: 227-246, 2009).

One of the most notable effects of increasing fibrillar tau in the brain is the gradual deterioration of short term memory; that is, the ability to recall immediately those memories only recently stored (P. Giannakopoulos et al., *Neurology* 60: 1495-1500, 2003). As there is no treatment for these disorders, it is important to find a novel invention that could target this pathogenic protein and improve memory deficits.

"Tangles" Accumulate in Brain in Traumatic Brain Injury (TBI), Concussions, Head Trauma and Chronic Traumatic Encephalopathy (CTE)

Brain "tangles" consisting of tau protein also accumulate progressively in the brain following blows to the head and include concussions, head injury, post-traumatic stress disorder (PTSD), and blast-induced traumatic brain injury (seen in soldiers and military personnel who have traumatic head injuries induced by a single blast). The movie "concussion" and the NFL Players Association all discuss the dementia-type behavior that has been seen in athletes following repeated concussions and/or blows to the head (known as traumatic brain injury or TBI). Loss of consciousness is a clinical hallmark of concussion but is not required to make the diagnosis. Other symptoms include confusion, disorientation, unsteadiness, dizziness, headache, and visual disturbances.

The long-term consequences to traumatic brain injury is referred to as Chronic Traumatic Encephalopathy (CTE), which is form of tauopathy (i.e. tau protein containing "tangles" in the brain). CTE is a progressive degenerative disease found in people who have suffered repeated brain trauma including sub-concussive hits to the head that do not cause immediate symptoms. The disease was previously called dementia pugilistica (DP), i.e. "punch-drunk" as it was initially found in those with a history of boxing. CTE has now been found in the brains of professional athletes including NFL athletes who play football, athletes prone to head injury including those that play ice hockey, rugby, skiing, skateboarding, stunt performing, bull riding, rodeo, and all other contact sports where participants experience repeated brain trauma. Individuals with CTE show many signs of dementia such as memory loss, aggression, confusion, and depression, which may appear years or many decades after the trauma. In September 2015, researchers with the Department of Veterans Affairs and Boston University announced they had identified CTE in 96% of NFL football players that they had examined and in 79% of all football players (Jason Breslow, New: 87 deceased NFL players test positive for brain disease. Frontline Jan. 9, 2016).

The neuropathology under a microscope is clear—there is primarily an accumulation of "tangles" that consist of tau protein, similar to the "tangles" seen in the brains of Alzheimer's disease patients. There is also some beta-amyloid protein deposition (i.e. "plaques"), but this is usually uncommon and less of a feature then the "tangle"

accumulation in brain. These findings suggest that blows to the head can lead to near immediate brain "tangle" accumulation that then leads to dementia-like symptoms including memory loss and cognitive decline. Identification of a nutraceutical that can help in the reduction and/or clearance of brain "tangles" would be an extraordinary supplement to take every day by all kinds of athletes, NFL players, the military and its soldiers.

SUMMARY OF THE INVENTION

Provided in one aspect is a composition comprising a therapeutically effective amount of a black currant extract; *Uncaria tomentosa* extract; and an oolong tea extract.

In some embodiments, the black currant extract comprises from about 10% to about 35% w/w proanthocyanidins, anthocyanidins, anthocyanins, or a combination thereof. In some embodiments, the black currant extract comprises about 25% w/w proanthocyanidins, anthocyanidins, anthocyanins, or a combination thereof. In some embodiments, the composition comprises from about 10 mg to about 100 mg of black currant extract. In some embodiments, the composition comprises from about 1% to about 10% w/w black currant extract. In some embodiments, the composition comprises from about 100 mg to about 500 mg of *Uncaria tomentosa* extract. In some embodiments, the composition comprises from about 10% to about 40% w/w *Uncaria tomentosa* extract. In some embodiments, the composition comprises from about 100 mg to about 500 mg of oolong tea extract. In some embodiments, the composition comprises from about 10% to about 40% w/w of oolong tea extract. In some embodiments, the composition is formulated as a pill, tablet, caplet, soft or hard gelatin capsule, lozenge, sachet, cachet, vegicap, liquid drop, elixir, suspension, emulsion, solution, beverage preparation, cold or hot tea beverage, syrup, tea bag, aerosol, suppository, sterile injectable solution, or sterile packaged powder. In some embodiments, the composition is formulated as a capsule. In some embodiments, the capsule is from about 200 mg to about 1000 mg.

Also provided in another aspect is a composition comprising a therapeutically effective amount of a black currant extract.

In some embodiments, the black currant extract comprises from about 10% to about 35% w/w proanthocyanidins, anthocyanidins, anthocyanins, or a combination thereof. In some embodiments, the black currant extract comprises about 25% w/w proanthocyanidins, anthocyanidins, anthocyanins, or a combination thereof. In some embodiments, the composition comprises from about 10 mg to about 100 mg of black currant extract. In some embodiments, the composition comprises from about 1% to about 10% w/w black currant extract. In some embodiments, the composition further comprises a therapeutically effective amount of *Uncaria tomentosa* extract. In some embodiments, the composition comprises from about 100 mg to about 500 mg of *Uncaria tomentosa* extract. In some embodiments, the composition comprises from about 10% to about 40% w/w *Uncaria tomentosa* extract. In some embodiments, the composition further comprises a therapeutically effective amount of oolong tea extract. In some embodiments, the composition comprises from about 100 mg to about 500 mg of oolong tea extract. In some embodiments, the composition comprises from about 10% to about 40% w/w of oolong tea extract. In some embodiments, the composition is formulated as a pill, tablet, caplet, soft or hard gelatin capsule, lozenge, sachet, cachet, vegicap, liquid drop, elixir, suspension, emulsion, solution, beverage preparation, cold or hot tea beverage, syrup, tea bag, aerosol, suppository, sterile injectable solution, or sterile packaged powder. In some embodiments, the composition is formulated as a capsule. In some embodiments, the capsule is from about 200 mg to about 1000 mg. In embodiments, the composition is more soluble than a composition comprising *Uncaria tomentosa* extract; oolong tea extract; and no black currant extract.

Also provided in another aspect is a method for the treatment of amyloidosis in a mammal in need thereof comprising administering to the mammal in need thereof any one of the compositions described herein.

In some embodiments, the amyloidosis is Alzheimer's disease, Down's syndrome, dementia pugilistica, cognitive dysfunction syndrome, canine cognitive dysfunction, multiple system atrophy, inclusion body myositosis, hereditary cerebral hemorrhage with amyloidosis of the Dutch type, Nieman-Pick disease type C, cerebral-amyloid angiopathy, dementia associated with cortical basal degeneration, the amyloidosis of type 2 diabetes, amyloidosis of chronic inflammation, amyloidosis of malignancy and Familial Mediterranean Fever, amyloidosis of multiple myeloma and B-cell dyscrasias, amyloidosis of prion diseases, Creutzfeldt-Jakob disease, Gerstmann-Straussler syndrome, kuru, scrapie, amyloidosis associated with carpal tunnel syndrome, senile cardiac amyloidosis, familial amyloidotic polyneuropathy, or amyloidosis associated with endocrine tumors.

In another aspect is provided a method of treating the formation, deposition, accumulation, or persistence of amyloid fibrils, comprising treating the fibrils with any one of the compositions described herein.

In another aspect is provided a method of treating the formation, deposition, accumulation, or persistence of beta-amyloid containing plaques, comprising treating the plaques with any one of the compositions described herein.

In another aspect is provided a method for the treatment of a tauopathy in a human or mammal in need thereof comprising administrating to the human or mammal in need thereof with any one of the compositions described herein.

In some embodiments, the tauopathy is Alzheimer's disease, frontotemporal lobar degeneration with that inclusions (FLTD-tau), Pick's disease, progressive supranuclear palsy, corticobasal degeneration, agryophlic grain disease, prion disease, amyotrophic lateral sclerosis-parkinsonism-dementia complex of Guam (also called Lytico Bodig disease), Parkinson's disease, tangle-predominant dementia, ganglioma, ganglioglioma, gangliocytoma, meningiomatosis, subacute sclerosing panencephalitis, lead encephalopathy, tuberous sclerosis, Hallervorden-Spatz disease, lipofuscinosis, traumatic brain injury (TBI), chronic traumatic encephalopathy (CTE), dementia pugilistic, concussion, single or repeated blows to the head, or post-traumatic stress disorder.

In another aspect is a method of treating the formation, deposition, accumulation, or persistence of tau protein containing tangles, comprising treating the tangles with any of the compositions described herein.

In another aspect is a method of treating the formation, deposition, accumulation, or persistence of tau protein containing plaques, comprising treating the plaques with any of the compositions described herein.

In one aspect is a method for improving cognitive performance and/or slowing cognitive decline in a subject in need thereof comprising administering to the subject any one of the compositions described herein to reduce formation, deposition, accumulation or persistence of beta-amyloid protein plaques or fibrils in the subject.

In some embodiments, the subject is a patient suffering from an amyloid disease.

Also provided in one aspect is a method for improving learning, memory, cognition, focus and/or concentration in a subject in need thereof comprising administering to the subject any one of the compositions described herein.

In some embodiments, the subject is patient with age-associated memory impairment (AAMI), mild cognitive impairment (MCI) or Alzheimer's disease.

Provided in another aspect is a method for inhibiting preventing, reducing, or treating tangles in the brain of a subject in need thereof comprising administering to the subject any one of the compositions described herein.

In some embodiments, the subject is a patient who has experienced single- or multiple concussions, traumatic brain injury (TBI), blows to the head, chronic traumatic encephalopathy (CTE), post-traumatic stress disorder, brain aging, mild-cognitive impairment or Alzheimer's disease.

Provided in another aspect is a method for preventing, reducing or treating plaques and tangles in the brain of an aged dog or cat, the method comprising treating the plaques and tangles with any one of the compositions described herein.

Provided in another aspect is a method for improving cognitive performance and/or slowing cognitive decline in an aged dog or cat suffering from brain formation, deposition, accumulation and/or persistence of plaques and tangles, comprising administering to the aged dog or cat any one of the compositions described herein.

Provided in another aspect is a method for improving athletic performance in a subject by inhibiting or reducing tangles in the brain comprising administering to the subject any one of the compositions described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A, 2B, and 2C depict representative images of Congo red, Thioflavin S, and electron micrographs of Aβ fibrils+/−LOTE and PTI-00703®.

FIGS. 5A, 5B, 5C, 5D, 5E, 5F, and 5G depict data from various internal tests to characterize TauRD fibrils for screening of tau aggregation inhibitors.

FIG. 17A demonstrates the dissolution of a single capsule of a cat's claw/oolong tea extract within a few seconds into water. FIG. 17B demonstrates the dissolution of a single capsule of cat's claw/oolong tea/black currant within a few seconds into water. Note both solutions contain initially clumps at the top of the glass of water. FIG. 17C demonstrates that within 10-15 seconds the cat's claw/oolong tea/black currant combination starts to self-dissolve in water.

FIG. 18A demonstrates the surprising discovery that addition of black currant makes the cat's claw/oolong tea extract more water soluble and is much better in taste. FIG. 18B demonstrates that the cat's claw/oolong tea extract still contains much water insoluble material that floats to the top of the glass. FIG. 18C demonstrates that the addition of black currant makes the cat's claw/oolong tea extract much more water soluble with little to no insoluble material at the top of the glass.

DETAILED DESCRIPTION OF THE INVENTION

Figure 1:
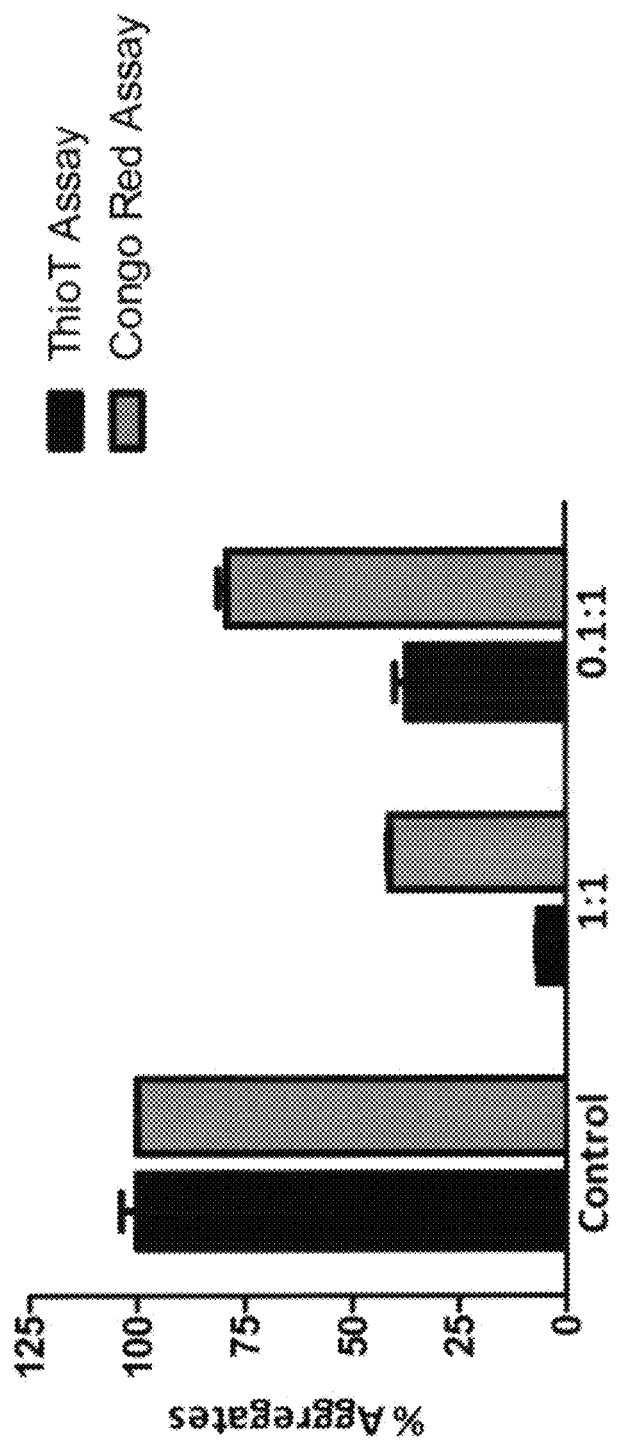
FIG. 1 depicts a graph of Aβ 1-42 aggregation measured by Thioflavin T fluorometry and Congo red binding after incubation with oolong tea extract (LOTE) and PTI-00703®.

Provided herein in one aspect is a composition comprising black currant extract, *Uncaria tomentosa* extract, and an oolong tea extract. The composition is useful for treating human subjects with Tauopathies, amyloid diseases, "plaques and/or tangles" in the brain, and those with traumatic brain injury (TBI), concussions (as observed in most athletes and the military/soldiers), post-traumatic stress disorders, head trauma, blows to the head (either single or repeated), and chronic traumatic encephalopathy (CTE).

In some embodiments, the composition effectively inhibits amyloid fibril formation, inhibits amyloid fibril growth, and/or causes dissolution and/or disruption of preformed amyloid fibrils. In some embodiments, the composition inhibits tau fibril formation (important for subjects in early- to mid-stage tauopathy); inhibits tau fibril growth (important for subjects in early- to mid-stage tauopathy), and/or causes the dissolution/disruption of preformed tau fibrils (important for late-stage tauopathy). In some embodiments, the composition is useful for the development of a cognition and memory supplement, to prevent, reduce and/or clear brain "plaques and tangles" in humans.

This disclosure recognizes that the amount of proanthocyanidins, anthocyanidins, anthocyanins, or a combination thereof present in the black currant extract is important for the activity described herein. In some embodiments, the black current extract comprises from about 10% to about 35% w/w proanthocyanidins, anthocyanidins, anthocyanins, or a combination thereof by weight, preferably about 25% w/w proanthocyanidins, anthocyanidins, anthocyanins, or a combination. This disclosure also recognizes that various plant extracts, even from the same plant source have differing effectiveness for dissolving plaques and tangles, such as oolong tea extract. In some embodiments, the oolong tea extract is LOTE. In some embodiments, the oolong tea extract is MemorTea®. In some embodiments, the oolong tea extract is obtained from the Guan Yin mountains of China and is provided by AuNutra Industries, Chino, Calif. In some embodiments, the composition comprising black currant extract, *Uncaria tomentosa* extract and an oolong tea extract provides a surprising and unexpected activity compared to other plant extracts or with each extract alone. In some embodiments, the combination of black currant extract, *Uncaria tomentosa* extract, and an oolong tea extract provides a synergistic or supplemental efficacy.

Definitions

Unless defined otherwise, all technical and scientific terms used herein have the meaning commonly understood by a person skilled in the art to which this disclosure belongs. As used herein, the following terms have the meanings ascribed to them below, unless specified otherwise. The terminology used herein is for the purpose of describing particular embodiments only and is not intended to be limiting of the disclosure.

As used herein, the singular forms "a", "an" and "the" are intended to include the plural forms as well, unless the context clearly indicates otherwise.

As used herein, the terms "about" when used to modify a numeric value or numeric range, indicate that deviations of 5% to 10% above and 5% to 10% below the value or range remain within the intended meaning of the recited value or range.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

"Comprising" shall mean that the methods and compositions include the recited elements, but not exclude others. "Consisting essentially of" when used to define methods and compositions, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transitional terms and phrases are within the scope of this invention.

A "therapeutically effective amount" in general means the amount that, when administered to a subject or animal for treating a disease, is sufficient to affect the desired degree of treatment for the disease. A "therapeutically effective amount" or a "therapeutically effective dosage" preferably inhibits, reduces, disrupts, disassembles tau fibril formation, deposition, accumulation and/or persistence, or treats a disease associated with these conditions, such as a tauopathy, by at least 20%, more preferably by at least 40%, even more preferably by at least 60%, and still more preferably by at least 80%, relative to an untreated subject. Effective amounts of a compound of this invention or composition thereof for treatment of a mammalian subject are about 0.1 to about 1000 mg/Kg of body weight of the subject/day, such as from about 1 to about 100 mg/Kg/day, especially from about 10 to about 100 mg/Kg/day. A broad range of disclosed composition dosages are believed to be both safe and effective.

"Anthocyanidins" are the sugar-free counterparts of anthocyanins. Examples of anthocyanidins include, but are not limited to, cyanidin, delphinidin, pelargonidin, peonidin, malvidin, and petunidin.

"Anthocyanins" are colored water-soluble pigments belonging to the phenolic group. Anthocyanins are based on the flavylium ion or 2-phenylchromenylium. Examples of anthocyanins, include but are not limited to, the glycosides of cyanidin, delphinidin, malvidin, pelargonidin, peonidin, and petunidin. Such examples include but are not limited to delphinidin-3-O-glucoside, delphinidin-3-O-rutinoside, cyanidin-3-O-glucoside, and cyanidin-3-O-rutinoside.

"Amyloid diseases" or "amyloidosis" suitable for treatment with the compositions of this inventions are diseases associated with the formation, deposition, accumulation, and/or persistence of amyloid fibrils, especially the fibrils of an amyloid protein selected from the group consisting of beta-amyloid protein or AP, AA amyloid, AL amyloid, IAPP amyloid, PrP amyloid, α2-microglobulin amyloid, transthyretin, prealbumin, and procalcitonin, especially Aβ and IAPP amyloid, Suitable such diseases include Alzheimer's disease, Down's syndrome, Mild cognitive impairment (MCI), Cognitive Canine Dysfunction (CDD), traumatic brain injury (TBI), chronic traumatic encephalopathy (CTE), concussions, hear trauma, single- and multiple blows to the head, post-traumatic stress disorders, dementia pugilistica, multiple system atrophy, inclusion body myositosis, hereditary cerebral hemorrhage with amyloidosis of the Dutch type, Nieman-Pick disease type C, cerebral β-amyloid angiopathy, dementia associated with cortical basal degeneration, the amyloidosis of type 2 diabetes, the amyloidosis of chronic inflammation, the amyloidosis of malignancy and Familial Mediterranean Fever, the amyloidosis of multiple myeloma and B-cell dyscrasias, the amyloidosis of prion diseases, Creutzfeldt-Jakob disease, Gertsmann-Straussler syndrome, kuru, scrapie, the amyloidosis associated with carpal tunnel syndrome, senile cardiac amyloidosis, familial amyloidotic polyneuropathy, and the amyloidosis associated with endocrine tumors.

"Fibrillogenesis" refers to the formation, deposition, accumulation and/or persistence of tau fibrils, filaments, inclusions, deposits, inclusions, or the like.

"Inhibition of fibrillogenesis" refers to the inhibition of formation, deposition, accumulation and/or persistence of such amyloid "plaque" or tau "tangle" fibril-like deposits.

"Disruption of fibrils or fibrillogenesis" refers to the disruption of preformed beta-amyloid or tau fibrils that usually exist in a pre-dominant β-sheet secondary structure. Such disruption by compounds of the invention may involve marked reduction or disassembly of beta-amyloid or tau fibrils as assessed by various methods such as circular dichroism spectroscopy, Thioflavin S fluorometry, SDS-PAGE/Western blotting, or negative stain electron microscopy, as demonstrated by the Examples presented in this application.

"Mammal" includes both humans and non-human mammals, such as companion animals (dogs, cats and the like), laboratory animals (such as mice, rats, guinea pigs, and the like) and farm animals (cattle, horses, sheep, goats, swine, and the like). In some embodiments, the mammal is a human. In some embodiments, the mammal is a dog or a cat.

"Plaques" refer to the meatball looking "amyloid deposits" consisting of beta-amyloid protein or Aβ found in various regions of brain (including hippocampus, cerebral cortex, frontal cortex etc.) that is a pathological hallmark of brain aging, mild-cognitive impairment (MCI), Alzheimer's disease, and is found in aging mammals such as dogs, cats (referred to as Cognitive Canine Dysfunction or CDD), monkeys, polar bears, horses and the like. Accumulation of amyloid "plaques" in brain is believed to lead to neurodegeneration, loss of synapses and connections between neurons, cognitive decline, memory decline and loss, and loss of focus and concentration.

"Proanthocyanidins" are oligomeric flavonoids. Proanthocyanidins include dimers or oligomers of catechin and epicatechin and their gallic acid esters.

The term "subject" as used herein, refers to an animal which is the object of treatment, observation or experiment. By way of example only, a subject may be, but is not limited to, a mammal including, but not limited to, a human, a cat, or a dog. In some embodiments, the subject is a human. In some embodiments, the human subject is a patient. In some embodiments, the subject is a cat. In some embodiments, the subject is a dog.

"Tangles" refer to the "dried-up" spaghetti looking "tangle-deposits" consisting of tau protein found in various regions of brain (including hippocampus, cerebral cortex, frontal cortex etc.) that is a pathological hallmark of brain aging, mild-cognitive impairment, Alzheimer's disease, concussions, traumatic brain injury (TBI), single and repeated blows to the head, post-traumatic stress disorders, chronic traumatic encephalopathy (CTE) and the like.

"Tauopathies" suitable for treatment with the compounds of this invention are also diseases associated with the formation, deposition, accumulation, or persistence of tau fibrils. Suitable diseases include Alzheimer's disease, frontotemporal lobar degeneration with tau inclusions (FTLD-tau) such as Pick's disease, progressive supranuclear palsy, and corticobasal degeneration, agyrophillic grain disease, some prion diseases, amyotrophic lateral sclerosis/parkinsonism-dementia complex of Guam (also called Lytico Bodig disease), dementia pugilistica, chronic traumatic encephalopathy, Parkinson's disease and particularly some genetic forms of Parkinson's disease, tangle-predominant dementia (with neurofibrillary tangles similar to Alzheimer's disease, but without amyloid plaques).

Tau fibrils is a generic term referring to a group of diverse, but specific intracellular or extracellular protein deposits which all have common morphological properties, staining characteristics, and x-ray diffraction spectra.

"Treating" or "treatment" of a disease includes preventing the disease from occurring in a mammal that may be predisposed to the disease but does not yet experience or exhibit symptoms of the disease (prophylactic treatment). Treatment can also mean inhibiting the disease (slowing or arresting its development), providing relief from the symptoms or side-effects of the disease (including palliative treatment), and relieving the disease (causing regression of the disease), such as by disruption of preformed tau fibrils. Treatment does not need be absolute. One such preventive treatment may be use of the disclosed compounds for the treatment of Mild Cognitive impairment (MCI).

Compositions

Provided in one aspect is a composition comprising a therapeutically effective amount of black currant extract, a therapeutically effective amount *Uncaria tomentosa* extract, and a therapeutically effective amount of an oolong tea extract.

Provided in one aspect is a composition consisting of a therapeutically effective amount of black currant extract, a therapeutically effective amount *Uncaria tomentosa* extract, a therapeutically effective amount of an oolong tea extract, and one or more pharmaceutically acceptable excipients or carriers.

Provided in one aspect is a composition consisting essentially of a therapeutically effective amount of black currant extract, a therapeutically effective amount *Uncaria tomentosa* extract, a therapeutically effective amount of an oolong tea extract, and one or more pharmaceutically acceptable excipients or carriers.

Provided in one aspect is a composition comprising a therapeutically effective amount of black currant extract. In some embodiments, the composition further comprises a therapeutically effective amount of *Uncaria tomentosa* extract. In some embodiments, the composition further comprises a therapeutically effective amount of an oolong tea extract. In some embodiments, the composition further comprises a therapeutically effective amount of *Uncaria tomentosa* extract and a therapeutically effective amount of an oolong tea extract.

In some embodiments, the compositions described herein to benefit human subjects with amyloidosis, and aged mammals (such as dogs and cats that develop amyloid "plaques" in the brain as they age). In some embodiments, the compositions described herein are useful for the treatment/inhibition of amyloid deposition, accumulation and/or persistence in amyloidosis. In some embodiments, the compositions described herein are useful for the inhibition of tau fibril formation, deposition, accumulation, and/or persistence.

In some embodiments, the compositions comprising the extracts described herein inhibit tau fibril formation more any one of the extracts alone, and also has the ability to rapidly disaggregate preformed tau fibrils. In some embodiments, the compositions comprising the extracts described herein inhibit amyloid fibril formation more any one of the extracts alone, and also has the ability to rapidly disaggregate preformed amyloid fibrils.

In some embodiments, the compositions described herein fibril inhibitory activity or efficacy greater than about 50%, greater than about 55%, greater than about 60%, greater than about 65%, greater than about 70%, greater than about 75%, greater than about 80%, greater than about 85%, greater than about 90%, greater than about 95%, or greater than about 99%.

In some embodiments, the compositions are formulated into a single dosage form, such as a capsule. In some embodiments, the capsule is from about 100 mg to about 2000 mg. In some embodiments, the capsule is from about 100 mg to about 1000 mg. In some embodiments, the capsule is from about 200 mg to about 2000 mg. In some embodiments, the capsule is from about 200 mg to about 1000 mg. In some embodiments, the capsule is about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 670 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1050 mg, about 1200 mg, about 1250 mg, about 1300 mg, about 1350 mg, about 1400 mg, about 1450 mg, about 1500 mg, about 1600 mg, about 1700 mg, about 1800 mg, about 1900 mg, or about 2000 mg.

Black Currant

Grown for its berries, black currant (*Ribes nigrum*) is a woody shrub from the family Grossulariaceae. It is native to temperate parts of central and northern Europe, New Zealand, and northern Asia and is widely cultivated both commercially and domestically. Aside from a high content of vitamin C, the berries contain flavonoids as well as at least 15 different phenolic acids, which include anthocyanins, anthocyanidins, and proanthocyanidins. The major anthocyanins that have been identified from black currant include delphinidin-3-O-glucoside, delphinidin-3-O-rutinoside, cyanidin-3-O-glucoside, and cyanidin-3-O-rutinoside.

This present disclosure recognizes that the amount of anthocyanins, anthocyanidins, proanthocyanidins, or a combination thereof present in the black currant extract is important for activity. In some embodiments, the black currant extract comprises from about 10% to about 35% w/w proanthocyanidins, anthocyanidins, anthocyanins, or a combination thereof. In some embodiments, the black currant extract comprises greater than 15% w/w proanthocyanidins, anthocyanidins, anthocyanins, or a combination thereof. In some embodiments, the black currant extract comprises from about 15% to about 35% w/w proanthocyanidins, anthocyanidins, anthocyanins, or a combination thereof. In some embodiments, the black currant extract comprises any one of from about 15% to about 30%, about 15% to about 25%, about 15% to 20%, about 20% to about 35%, and about 20% to about 30 w/w proanthocyanidins, anthocyanidins, anthocyanins, or a combination thereof. In some embodiments, the black currant extract comprises about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, or about 35% w/w proanthocyanidins, anthocyanidins, anthocyanins, or a combination thereof. In some embodiments, the black currant extract comprises about 25% w/w proanthocyanidins, anthocyanidins, anthocyanins, or a combination thereof. In some embodiments, the black currant extract comprises from about 20% to about 30% w/w proanthocyanidins, anthocyanidins, anthocyanins, or a combination thereof. In some embodiments, the black currant extract comprises from about 15% to about 35% w/w proanthocyanidins, anthocyanidins, anthocyanins, or a combination thereof.

In some embodiments, the black currant extract comprises anthocyanins, anthocyanidins, proanthocyanidins, or a combination thereof. In some embodiments, the black currant extract comprises anthocyanins. In some embodiments, the black currant extract comprises anthocyanidins. In some embodiments, the black currant extract comprises proanthocyanidins. In some embodiments, the black currant extract comprises a combination of anthocyanins, anthocyanidins, and/or proanthocyanidins.

In some embodiments, the composition comprises from about 10 mg to about 500 mg of black currant extract. In some embodiments, the composition comprises from about 10 mg to about 250 mg of black currant extract. In some embodiments, the composition comprises from about 10 mg to about 100 mg of black currant extract. In some embodiments, the composition comprises from about 30 mg to about 100 mg of black currant extract. In some embodiments, the composition comprises about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 300 mg, about 350 mg, about 400 mg, about 450 mg, or about 500 mg of black currant extract.

In some embodiments, the composition comprises from about 0.1% to about 30% w/w black currant extract. In some embodiments, the composition comprises from about 0.1% to about 20% w/w black currant extract. In some embodiments, the composition comprises from about 0.1% to about 10% w/w black currant extract. In some embodiments, the composition comprises from about 1% to about 30% w/w black currant extract. In some embodiments, the composition comprises from about 1% to about 20% w/w black currant extract. In some embodiments, the composition comprises from about 1% to about 10% w/w black currant extract. In some embodiments, the composition comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% w/w black currant extract.

Cat's Claw

The plant *Uncaria tomentosa*, also known as "Uña de Gato" (in Spanish) or "Cat's claw" (in English) refers to a woody vine which grows within the Amazon rain forest. Other names for Cat's claw also include Paraguayo, Garabato, Garbato casha, Tambor huasca, Una de gavilan, Hawk's claw, Nail of Cat, and Nail of Cat Schuler. This slow-growing vine takes 20 years to reach maturity and can grow over 100 feet in length as it attaches and wraps itself around the native trees. It is found abundantly in the foothills, at elevations of two to eight thousand feet. The vine is referred to as "cat's claw" because of its distinctive curved claw-like thorns that project from the base of its leaves. *Uncaria tomentosa* is expected to have immune-supporting, anti-inflammatory, anti-viral, anti-mutagenic and antioxidant properties. The anti-inflammatory properties, for example, are expected to be beneficial for the treatment of arthritis, rheumatism, bursitis and gout. Without being bound by theory, it is believed that is beneficial effects in treating arthritis pain can be due, in part, to its ability to cleanse the digestive tract and aid in removing toxins from the body. Furthermore, *Uncaria tomentosa* or cat's claw is expected to alleviate pain, and is expected to be helpful in reducing pain associated with, for example, chemotherapy, radiation treatment and AZT use.

*Uncaria tomentosa* or cat's claw is also expected to be useful in stopping viral infections in stopping viral infections in the early stages, fighting opportunistic infections in AIDs patients and decreasing the viable size of some skin tumors and cysts. *Uncaria tomentosa* can also be used to treat a variety of ailments, including cancer, AIDs, Crohn's disease, respiratory infections, allergies, herpes, prostrate problems, lupus, Epstein Barr virus, chronic fatigue syndrome, and a variety of stomach and bowl disorders.

For additional and further information and background on *Uncaria tomentosa*, the reader is also referred to the inventors' WIPO International publication number WO98/51302, which is incorporated herein by reference in its entirety.

We have earlier discovered and disclosed a naturally occurring plant product, the inner bark and/or roots from the plant *Uncaria tomentosa*, or Cat's Claw, that we call PTI-00703®, in WIPO International publication number WO98/51302 entitled 'Composition and Methods for Treating Alzheimer's Disease and other Amyloidoses' dated Nov. 19, 1998, which is incorporated herein by reference in its entirety. As disclosed therein, this plant compound alone has surprising efficacy in disrupting and/or dissolving amyloid deposits and other accumulations, and is believed to be a potent inhibitor of amyloid formation in Alzheimer's disease, Type II Diabetes, and other amyloidoses.

The *Uncaria tomentosa* extract PTI-00703® is also referred to as '703' or 'PTI-703' for the therapeutic intervention of amyloidosis. PTI-00703® is derived from cat's claw bark found in the Amazon rainforest. In some embodiments, the *Uncaria tomentosa* extract is PTI-00703. In some embodiments, the *Uncaria tomentosa* extract is derived from the inner bark and/or roots. In some embodiments, the *Uncaria tomentosa* extract is derived from the inner bark and/or roots from the Amazon rainforest.

In some embodiments, the composition comprises from about 100 mg to about 500 mg of *Uncaria tomentosa* extract. In some embodiments, the composition comprises from about 100 mg to about 300 mg of *Uncaria tomentosa* extract. In some embodiments, the composition comprises from about 100 mg to about 250 mg of *Uncaria tomentosa* extract. In some embodiments, the composition comprises about 100 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, or about 500 mg of *Uncaria tomentosa* extract.

In some embodiments, the composition comprises from about 5% to about 60% w/w *Uncaria tomentosa* extract. In some embodiments, the composition comprises from about 5% to about 40% w/w *Uncaria tomentosa* extract. In some embodiments, the composition comprises from about 10% to about 60% w/w *Uncaria tomentosa* extract. In some embodiments, the composition comprises from about 10% to about 40% w/w *Uncaria tomentosa* extract. In some embodiments, the composition comprises about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% w/w *Uncaria tomentosa* extract.

Oolong Tea

Oolong tea is a Chinese tea (*Camellia sinensis*) produced through a process including withering the plant under strong sun and oxidation before curling and twisting. Over 25 extracts of teas, along with extracts of coffee and yerba mate, were screened by the present Inventors for amyloid fibril aggregation inhibition and disaggregation in vitro using a variety of assays. The present Inventors recognized that the use of an oolong tea extract in combination with *Uncaria tomentosa* extract exhibited amyloid fibril aggregation inhibition and disaggregation. In some embodiments, the oolong tea extract is LOTE. In some embodiments, the oolong tea extract is MemorTea®. In some embodiments, the oolong tea extract is obtained from the Guan Yin mountains of China and is provided by AuNutra Industries, Chino, Calif.

In some embodiments, the composition comprises from about 100 mg to about 500 mg of oolong tea extract. In some embodiments, the composition comprises from about 100 mg to about 250 mg of oolong tea extract. In some embodiments, the composition comprises from about 100 mg to about 300 mg of oolong tea extract. In some embodiments, the composition comprises about 100 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg of oolong tea extract.

In some embodiments, the composition comprises from about 5% to about 60% w/w oolong tea extract. In some embodiments, the composition comprises from about 5% to about 40% w/w oolong tea extract. In some embodiments, the composition comprises from about 10% to about 60% w/w oolong tea extract. In some embodiments, the composition comprises from about 10% to about 40% w/w oolong tea extract. In some embodiments, the composition comprises about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60% w/w oolong tea extract.

In some exemplary embodiments, the composition comprises 1% to 20% w/w black currant extract with 25% anthocyanins, 10% to 50% w/w *Uncaria tomentosa* extract, and 10% to 50% w/w oolong tea extract. In some exemplary embodiments, the composition comprises 1% to 15% w/w black currant extract with 25% anthocyanins, 10% to 45% w/w *Uncaria tomentosa* extract, and 10% to 45% w/w oolong tea extract. In some exemplary embodiments, the composition comprises 1% to 10% w/w black currant extract with 25% anthocyanins, 10% to 40% w/w *Uncaria tomentosa* extract, and 10% to 40% w/w oolong tea extract. In some exemplary embodiments, the composition comprises 1% to 10% w/w black currant extract with 25% anthocyanins, 20% to 40% w/w *Uncaria tomentosa* extract, and 20% to 40% w/w oolong tea extract.

In some exemplary embodiments, the composition comprises black currant extract; *Uncaria tomentosa* extract, and oolong tea extract, wherein black currant extract, *Uncaria tomentosa* extract, and oolong tea extract are active components. In some embodiments, the black current extract comprises about 10% to about 35% w/w proanthocyanidins, anthocyanidins, anthocyanins, or a combination thereof. In some embodiments, the black current extract comprises about 25% w/w proanthocyanidins, anthocyanidins, anthocyanins, or a combination thereof. In some embodiments, the black currant is about 1% to 20% w/w, 1% to 15% w/w, or 1% to 10% w/w of the active components of the composition, wherein black currant extract, *Uncaria tomentosa* extract, and oolong tea extract are active components of the composition. In some embodiments, the *Uncaria tomentosa* extract is about 10% to 50% w/w, 10% to 45% w/w, 10% to 40% w/w, or about 20% to 40% w/w of the active components of the composition, wherein black currant extract, *Uncaria tomentosa* extract, and oolong tea extract are active components of the composition. In some embodiments, the oolong tea extract is about 10% to 50% w/w, 10% to 45% w/w, 10% to 40% w/w, or about 20% to 40% w/w of the active components of the composition, wherein black currant extract, *Uncaria tomentosa* extract, and oolong tea extract are active components of the composition.

Provided in one aspect is a blended composition comprising black currant extract, *Uncaria tomentosa* extract, and oolong tea extract that is more soluble (e.g. water soluble) than a blended composition that has no black currant extract, such as a composition comprising of *Uncaria tomentosa* extract and oolong tea extract as active agents. In blended composition comprising black currant extract, *Uncaria tomentosa* extract, and oolong tea extract that is more soluble (e.g. water soluble) than a blended composition that has no black currant extract, such as a composition consisting of *Uncaria tomentosa* extract and oolong tea extract. In some embodiments, the addition of black currant extract to a composition containing *Uncaria tomentosa* extract and oolong tea extract increases the water solubility of the *Uncaria tomentosa* extract and the oolong tea extract. In some embodiments, the addition of black currant extract to a composition containing *Uncaria tomentosa* extract and oolong tea extract increases the solubility (e.g. water solubility or aqueous solubility) of the *Uncaria tomentosa* extract and/or the oolong tea extract by at least 1-fold, at least 5-fold, at least 10-fold, at least 20-fold, at least 30-fold, at least 40, or at least 50, including 1-, 2-, 3-, 4-, 5-, 6-, 7-, 8-, 9-, 10-, 15-, 20-, 30-, 40-, 50-, 60-, 70-, 80-, 90-, or 100-fold. In some embodiments, the addition of black currant extract to a composition containing *Uncaria tomentosa* extract and oolong tea extract increases the solubility (e.g. water solubility or aqueous solubility) of the *Uncaria tomentosa* extract and/or the oolong tea extract by at least 1- to at least 50-fold or at least 1- to at least 20 fold, including about 1-, 2-, 3-, 4-, 5-, 6-, 7-, 8-, 9-, 10-, 15-, 20-, 30-, 40-, 50-, 60-, 70-, 80-, 90-, or 100-fold. In some embodiments, the addition of black currant extract to a composition containing *Uncaria tomentosa* extract and oolong tea extract increases the solubility (e.g. water solubility or aqueous solubility) of the *Uncaria tomentosa* extract and/or the oolong tea extract by at least 1-fold, at least 5-fold, at least 10-fold, at least 20-fold, at least 30-fold, at least 40, or at least 50, including 1-, 2-, 3-, 4-, 5-, 6-, 7-, 8-, 9-, 10-, 15-, 20-, 30-, 40-, 50-, 60-, 70-, 80-, 90-, or 100-fold greater than a composition with no black currant extract, such as a composition comprising *Uncaria tomentosa* extract and oolong tea extract as the only active agents. In some embodiments, the composition comprising black currant extract, *Uncaria tomentosa* extract, oolong tea extract has increased solubility (e.g. water solubility or aqueous solubility) of at least 1- to at least 50-fold or at least 1- to at least 20 fold, including about 1-, 2-, 3-, 4-, 5-, 6-, 7-, 8-, 9-, 10-, 15-, 20-, 30-, 40-, 50-, 60-, 70-, 80-, 90-, or 100-fold greater than a composition with no black currant extract, such as a composition comprising *Uncaria tomentosa* extract and oolong tea extract as the only active agents. In some embodiments the solubility (e.g., water solubility or aqueous solubility is increased by any one of from 1-fold to 50-fold, 5-fold to 50-fold, 5-fold to 40-fold, 5-fold to 30-fold, 5-fold to 20-fold, from 10-fold to 50-fold, from 10-fold to 40-fold, from 10-fold to 35-fold, from 10-fold to 30-fold, from 10-fold to 25-fold, and from 10-fold to 20-fold. This is a surprising discovery in that the *Uncaria tomentosa* extract and oolong tea extract (especially a *Uncaria tomentosa* extract) are very water-insoluble. The addition of black currant extract as a third ingredient surprisingly makes the resulting composition containing all three ingredients very water soluble and the ingredients taste much better (less astringent and less bitter). Making the ingredients more water-soluble with the addition of black currant also allows the final product provided to be made into a beverage, beverage shot and/or product for people who are unable to swallow pills, caplets, tablets, capsules or the like.

Uses

Provided in one aspect, the compositions described herein are useful for the development of a cognition and memory supplement, to inhibit, prevent, reduce and/or clear brain "plaques and/or tangles" in humans.

The compositions described herein also benefit aged dogs and cats, who develop brain "plaques" (and to a lesser extent, "tangles"), and have dementia as defined in Canine Cognitive Dysfunction (CCD).

Provided in another aspect, the compositions described herein are pet food supplements for aged dogs that reduce brain amyloid "plaques" and improve cognition, memory, short-term memory, focus and concentration.

Provided in another aspect, the compositions described herein are pet food supplements for aged cats that inhibit, prevent, and/or reduce brain amyloid "plaques" and improve cognition, memory, short-term memory, focus and concentration.

In another aspect, the compositions described herein are used for treating of tau fibril formation, deposition, accumulation and/or persistence, such as that which occurs in the tauopathies. In some embodiments, the compositions described herein are used for treating tauopathies to prevent and/or treat, for example, traumatic brain injury (TBI), concussions (as observed in most athletes and the military/soldiers), post-traumatic stress disorders, head trauma, blows to the head (either single or repeated), and chronic traumatic encephalopathy (CTE).

Provided in another aspect, the compositions described herein are effective inhibitors and/or reducers of brain "tangles," such as those found in people with traumatic brain injury (TBI), concussions (as observed in most athletes and the military/soldiers), post-traumatic stress disorders, head trauma, blows to the head (either single or repeated), and chronic traumatic encephalopathy (CTE).

Provided in another aspect, the compositions described herein effectively inhibit and/or prevent amyloid fibril formation, and/or prevent inhibit amyloid fibril growth, and/or cause dissolution and/or disruption of pre-formed amyloid fibrils.

Provided in another aspect, the compositions described herein prevent and/or inhibit of tau fibril formation (important for subjects in early- to mid-stage tauopathy), inhibit of tau fibril growth (important for subjects in early- to mid-stage tauopathy), and/or cause the dissolution/disruption of preformed tau fibrils (important for late-stage tauopathy).

Provided in another aspect, the compositions described herein inhibit tau fibril formation, inhibit tau fibril growth, inhibit tau fibril-proteoglycan interactions, inhibit tau fibril-proteoglycan and/or glycosaminoglycan interactions, and cause dissolution and/or disruption of preformed tau fibrils.

Methods

Provided in another aspect, is a method of the treatment of amyloidosis in a mammal in need thereof comprising administering to the mammal in need thereof any one of the compositions described herein. In some embodiments, the amyloidosis is Alzheimer's disease, Down's syndrome, dementia pugilistica, cognitive dysfunction syndrome, canine cognitive dysfunction, multiple system atrophy, inclusion body myositosis, hereditary cerebral hemorrhage with amyloidosis of the Dutch type, Nieman-Pick disease type C, cerebral-amyloid angiopathy, dementia associated with cortical basal degeneration, the amyloidosis of type 2 diabetes, amyloidosis of chronic inflammation, amyloidosis of malignancy and Familial Mediterranean Fever, amyloidosis of multiple myeloma and B-cell dyscrasias, amyloidosis of prion diseases, Creutzfeldt-Jakob disease, Gerstmann-Straussler syndrome, kuru, scrapie, amyloidosis associated with carpal tunnel syndrome, senile cardiac amyloidosis, familial amyloidotic polyneuropathy, or amyloidosis associated with endocrine tumors.

Also provided in one aspect is a method of treating the formation, deposition, accumulation, or persistence of amyloid fibrils, comprising treating the fibrils with any one of the compositions described herein.

Provided in another aspect is a method of treating the formation, deposition, accumulation, or persistence of beta-amyloid containing plaques, comprising treating the plaques with any one of the compositions described herein.

Provided in another aspect is a method for the treatment of a tauopathy in a human or mammal in need thereof comprising administrating to the human or mammal in need thereof comprising administering any one of the compositions described herein. In some embodiments, the tauopathy is Alzheimer's disease, frontotemporal lobar degeneration with that inclusions (FLTD-tau), Pick's disease, progressive supranuclear palsy, corticobasal degeneration, agryophlic grain disease, prion disease, amyotrophic lateral sclerosis-parkinsonism-dementia complex of Guam (also called Lytico Bodig disease), Parkinson's disease, tangle-predominant dementia, ganglioma, ganglioglioma, gangliocytoma, meningiomatosis, subacute sclerosing panencephalitis, lead encephalopathy, tuberous sclerosis, Hallervorden-Spatz disease, lipofuscinosis, traumatic brain injury (TBI), chronic traumatic encephalopathy (CTE), dementia pugilistic, concussion, single or repeated blows to the head, or post-traumatic stress disorder.

Provided in one aspect is a method of treating the formation, deposition, accumulation, or persistence of tau protein containing tangles, comprising treating the tangles with any one of the compositions described herein.

Provided in one aspect is a method for improving cognitive performance and/or slowing cognitive decline in a subject in need thereof comprising administering to the subject any one of the compositions described herein to reduce formation, deposition, accumulation or persistence of beta-amyloid protein plaques or fibrils in the subject.

Provided in one aspect is a method for improving cognitive performance and/or slowing cognitive decline in a subject suffering from an amyloid disease comprising administering to the subject any one of the compositions described herein to reduce formation, deposition, accumulation or persistence of beta-amyloid protein plaques or fibrils in the subject.

Provided in one aspect is a method for improving learning, memory, cognition, focus and/or concentration in a subject in need thereof comprising administering to the subject with any one of the compositions described herein.

Provided in one aspect is a method for improving learning, memory, cognition, focus and/or concentration in a subject with age-associated memory impairment (AAMI), mild cognitive impairment (MCI) or Alzheimer's disease comprising administering to the subject with any one of the compositions described herein.

Provided in one aspect is a method for preventing, reducing, or treating tangles in the brain of a subject in need thereof comprising administering to the subject any one of the compositions described herein.

Provided in one aspect is a method for preventing, reducing, or treating tangles in the brain of a subject who has experienced single- or multiple concussions, traumatic brain injury (TBI), blows to the head, chronic traumatic encephalopathy (CTE), post-traumatic stress disorder, brain aging, mild-cognitive impairment or Alzheimer's disease comprising administering to the subject any one of the compositions described herein.

Provided in one aspect is a method for preventing, reducing, or treating plaques in the brain of a subject in need thereof comprising administering to the subject any one of the compositions described herein.

Provided in one aspect is a method for preventing, reducing or treating plaques and tangles in the brain of an aged dog or cat, the method comprising treating the plaques and tangles with any one of the compositions described herein.

Provided in one aspect is a method for improving cognitive performance and/or slowing cognitive decline in an aged dog or cat suffering from brain formation, deposition, accumulation and/or persistence of plaques and tangles, comprising administering to the aged dog or cat a composition any one of the compositions described herein.

Provided in one aspect is a method for improving athletic performance in a subject by inhibiting or reducing tangles in the brain comprising administering to the subject any one of the compositions described herein. In some embodiments, the subject is an athlete.

Dosage

In some embodiments, the compositions have a therapeutically effective amount of the combination of black currant extract, an oolong tea extract, and *Uncaria tomentosa* extract, in a dosage in the range of from about 0.1 to about 500 mg/kg of body weight of the subject, and more preferably in the range from about 1.0 to about 100 mg/kg of body weight of the subject.

However, it will be understood that the therapeutic dosage administered will be determined by the physician in the light of the relevant circumstances including the clinical condition to be treated, the organ or tissues affected or suspected to be affected with tau fibril accumulation, and the chosen route of administration. Therefore, the above dosage ranges are not intended to limit the scope of the invention in any way.

The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

Administration

In general, the compositions described herein are by any of the usual modes known in the art. Administration can be by one of the following routes: oral, topical, and systemic (e.g. transdermal, intranasal or by suppository), or parenteral (e.g. intramuscular, subcutaneous, or intravenous injection). In some embodiments, the compositions are administered orally such as in oral capsules, beverage preparations, beverage shots, or any other method, or by aerosol spray or in a parenterally injectable or infusible form.

In some embodiments, the compositions are administered orally in the form of a beverage shot. A beverage shot as used herein is a beverage that contains any one of the compositions described herein in a small amount of liquid (such as about 50 mL). Or in other words, a beverage shot is a concentrated beverage drink.

Formulations

In some embodiments, the black currant extract, *Uncaria tomentosa* extract, and Oolong tea extract are formulated into a single dosage form. In some embodiments, any two of black currant extract *Uncaria tomentosa* extract, Oolong tea extract are formulated into a single dosage form. In some embodiments, any one of black currant extract *Uncaria tomentosa* extract, Oolong tea extract is formulated into a single dosage form.

Compositions can take the form of tablets, pills, capsules, semisolids, powders, sustained release formulations, solutions, beverages, beverage shots, suspensions, elixers, aerosals, or any other appropriate compositions, and comprise at least one pharmaceutically acceptable excipient, carrier, or diluent. Suitable excipients, carriers and diluents are well known to persons of ordinary skill in the art. The methods of formulating the compositions, can be found in standard references as Alfonso A R: Remington's Pharmaceutical Sciences, 17$^{th}$ ed., Mack Publishing Company, Easton, Pa., 1985. Suitable liquid carriers, especially for injectable solutions, include water, aqueous saline solution, aqueous dextrose solution, and glycols.

In particular, the compound(s) can be administered orally, for example, as tablets, trouches, lozenges, aqueous or oily suspensions, dispersible powders or granules, dissolving fizz tablets, emulsions, hard or soft capsules, syrups or elixers. In one embodiment, only one such compound is administered in any particular dosage form. Compositions intended for oral use can be prepared to any method known in the art for the manufacture of nutraceutical compositions and such compositions can contain one or more agents selected from the group consisting of sweetening agents, flavoring agents, coloring agents and preserving agents in order to provide nutraceutically elegant and palatable preparations.

In some embodiments, the components of the compositions are obtained commercially in any form could be further modulated using suitable carriers, excipients and diluents including lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed response of the active ingredient after administration to the subject.

Tablets containing the extracts described herein in admixture with non-toxic pharmaceutically acceptable excipients that are suitable for the manufacture of tablets. These excipients include, for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia; and lubricating agents, for example magnesium stearate or stearic acid or talc. The tablets can be uncoated or they can be coated by known techniques to delay disintegration and absorption in the gastrointestinal tract and thereby provide a sustained action over a longer period. For example, a time delay material such as glycerol monostearate or glycerol distearate can be employed. Formulations for oral use can also be prepared as hard gelatin capsules wherein the compounds are mixed with an inert solid diluent, for example, calcium carbonate, calcium phosphate or kaolin, or as soft gelatin capsules, wherein the active ingredient is mixed with water or an oil medium, for example, peanut oil, liquid paraffin or olive oil.

Aqueous suspensions contain the compound in admixture with excipients suitable for the manufacture of aqueous suspensions. Such excipients include, for example, suspending agents, for example, sodium carboxymethylcellulose, methylcellulose, hydroxypropylmethyl cellulose, sodium alginate, polyvinylpyrrolidone, gum tragacanth and gum acacia; and dispersing and wetting agents that are naturally occurring phosphatides, for example lecithin, or condensation products of an alkylene oxide with fatty acids; for example polyoxyethylene stearate, or condensation products of ethylene oxide with long chain aliphatic alcohols, for example heptadecaethyleneoxycetanol, or condensation products of ethylene oxide with partial esters derived from fatty acids such as hexitol, for example polyoxyethylene sorbitol monooleate, or condensation products of ethylene oxide with partial esters from fatty acids and a hexitol annyhydride, for example polyethylene sorbitan monooleate. The aqueous suspensions can also contain one or more preservatives, for example ethyl or n-propyl p-hydroxybenzoate, one or more coloring agents, one or more flavoring agents, and/or one or more sweetening agents, such as sucrose or saccharin.

Oily suspensions can be formulated by suspending the extracts in a vegetable oil, for example arachs oil, olive oil, sesame oil, or coconut oil, or in a mineral oil such as liquid paraffin. The oily suspensions can contain a thickening agent for example beeswax, hand paraffin or cetyl alcohol. Sweetening agents, such as those set forth below, and flavoring agents can be added to provide a palatable oral preparation. These compositions can be preserved by the addition of an antioxidant such as ascorbic acid.

Dispersible powders and granules suitable for preparation of an aqueous suspension by the addition of water provide the active ingredients in admixture with a dispersing or wetting agent, a suspending agent and one or more preservatives. Suitable dispersing or wetting agents and suspending agents are exemplified by those already described above. Additional excipients, for example sweetening, flavoring and agents, can also be present.

The compositions can also be in the form of oil-in-water emulsions. The oily phase of a vegetable oil, for example, olive oil or arachis oils, or a mineral oil, for example liquid paraffin, or mixtures thereof. Suitable emulsifying agents can be naturally-occurring gums, for example gum acacia or gum tragacanth, naturally occurring phosphatides, for example soy bean, lecithin, and esters or partial esters derived from fatty acids and hexitol anhydrides, for example sorbitan esters with ethylene oxide, for example polyoxyethylene sorbitan monooleate, and condensation products of the said partial esters with ethylene oxide, for example polyethylene sorbitan monooleate. The emulsion can also contain sweetening and flavoring agents. Syrups and elixers can be formulated with sweetening agents, for example, glycerol, sorbitol or sucrose. Such formulations can also contain a demulcent, a preservative and flavoring and coloring agents.

The following non-limiting Examples are given by way of illustration only and are not considered a limitation of this disclosure, many apparent variations of which are possible without departing from the spirit or scope thereof.

EXAMPLES

The present technology is further illustrated by the following Examples, which should not be construed as limiting in any way. The following Examples demonstrate the preparation, characterization, and use of the compositions described herein.

Composition—Component Preparation

For these studies, the oolong tea extract was prepared in accordance to the following procedure. To make tea extracts from tea leaves, 2 g of tea leaves were extracted into 100° C. deionized water for 20 min with occasional mixing. Tea extracts were filtered through a >10 μm cut-off filter to remove large particulates. Extracts were snap frozen in dry ice/ethanol then lyophilized to obtain a dried, concentrated powder. Dried powder was weighed and resuspended in DMSO to make concentrated 100 mg/ml stock solutions. Stock solutions were diluted into aggregation reactions such that DMSO concentration was less than 0.28% in the final reaction.

The oolong tea extract was prepared from oolong tea obtained from the Guan Yin mountains of China (MemorTea®; AuNutra Industries Inc., Chino, Calif.). PTI-00703® is a powder extract made from water extraction of the inner bark of *Uncaria tomentosa* obtained from the Amazon rainforest. Methods for preparing PTI-00703® have been described, for example in WIPO International Pub. No. WO98/51302. Black currant extract containing 25% anthocyanins is a powder extract prepared from European black currant fruit (Cassis fruit) and is obtained from Vitaquest, West Caldwell, N.J. Ethanol extracts of black currant, oolong tea and/or *Uncaria tomentosa* are within the scope of this disclosure.

Composition A containing oolong tea extract, *Uncaria tomentosa* extract, and black currant extract (25% anthocyanins) is prepared as follows. *Uncaria tomentosa* extract (PTI-00703®) was granulated first using acacia gum as a binding agent to provide 206 mg of granulated *Uncaria tomentosa* extract (187.5 mg of Cat's claw). Then an equal amount of an oolong tea extract (187.5 mg) was added followed by 50 mg of black currant extract (25% anthocyanins) to provide the test composition.

Example 1: Disruption/Inhibition of Alzheimer's Aβ Fibrils or Aggregates

The compositions described herein were found to be potent disrupter/inhibitors of Aβ protein fibrils or aggregates. This example studies the efficacy of the compositions to cause disassembly/disruption/disaggregation of pre-formed amyloid fibrils of Alzheimer's disease (i.e. consisting of Aβ 1-42) was analyzed.

Part A: Thioflavin T Fluorometry

In this study, Thioflavin T fluorometry was used to determine the effects of the compositions. Thioflavin T specifically binds to fibrillary amyloid, and this binding produces a fluorescence enhancement at 485 nm that is directly proportional to the number of amyloid fibrils formed. The higher the fluorescence, the greater the number of amyloid fibrils formed (Nakai et al., *Lab. Invest.* 65:104-110, 1991; Levine III, *Protein Sci.* 2:404-410, 1993; *Amyloid: Int. J. Exp. Clin. Invest.* 2:1-6, 1995).

In this study, 40 μl of a 1 mg/ml solution (in distilled water) or pre-fibrillized human Aβ 1-42 (rPeptide) was incubated at 37° C. for 3 days either alone (control), or in the presence of any one of the compositions disclosed herein (at Aβ:test composition weight ratios of 1:1, 1:0.1, 1:0.01, and 1:0.001). The final concentration of Aβ in the reaction was 0.4 mg/ml (88 μM) in phosphate-buffered saline (PBS), pH 7.4+0.02% sodium azide in 100 μl final volume. Following 3-days of co-incubation, 12.5 μl of each incubation mixture was transferred into a 96-well microtiter plate containing 37.5 μl of PBS and 200 μl of a Thioflavin T solution (i.e. 125 μM Thioflavin T in 62.5 mM phosphate buffer, pH 6.8). The emission fluorescence was read at 485 nm (444 nm excitation wavelength) using an ELISA plate fluorometer after subtraction with buffer alone or composition alone, as blank.

In the first set of studies, the following compositions were tested:

| Composition No | Components |
| --- | --- |
| 11.1 | Oolong tea extract (MemorTea ®) + *Uncaria tomentosa* extract (PTI-00703 ®) (1:1) |
| 11.2 | *Uncaria tomentosa* extract (PTI-00703 ®) |
| 11.3 | Peruvian *Uncaria tomentosa* extract (Vitaquest, West Caldwell, NJ) |
| 11.4 | Vision Smart Supreme ® (contains 210 mg anthocyanins from black currant extract per 2 capsules; Vision Smart Center, Los Angeles, CA) |
| 11.5 | Euro Black currant (*Ribes Nigrum*) extract powder with 25% anthocyanins (Vitaquest, West Caldwell, NJ). |
| 11.6 | Black currant (*Ribes Nigrum*) extract powder with 15% anthocyanins (Vitaquest, West Caldwell, NJ). |
| 11.7 | Prevagen ® (contains 10 mg apoaequorin per each capsule; Quincy Bioscience, Madison, W.I.) |

Figure 11:
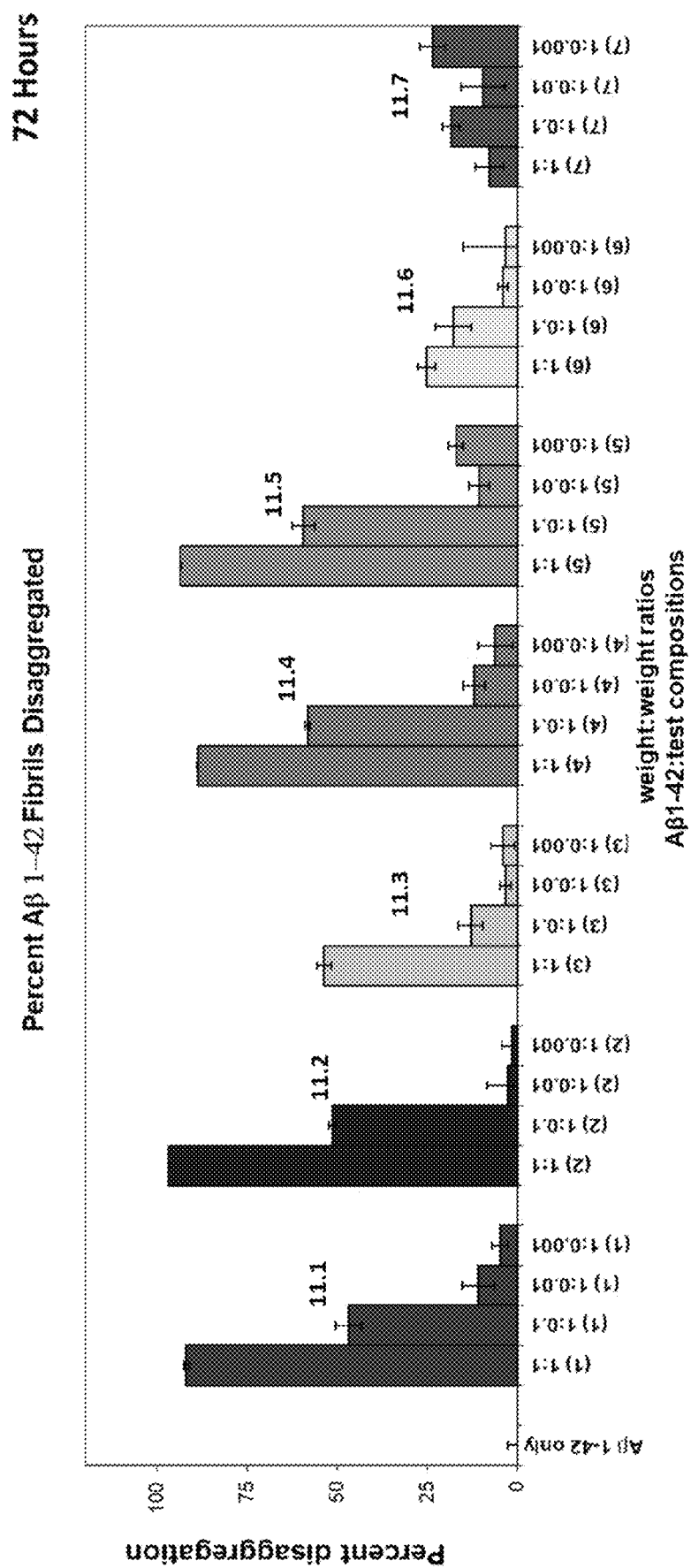
FIG. 11 depicts the graph of Aβ 1-42 aggregation measured by Thioflavin T fluorometry after incubation with: Composition 11.1; Composition 11.2; Composition 11.3; Composition 11.4, Composition 11.5, Composition 11.6, and Composition 11.7.

FIG. 11 shows the results of the 3-day incubation with the following compositions: Composition 11.1; Composition 11.2; Composition 11.3; Composition 11.4, Composition 11.5, Composition 11.6, and Composition 11.7.

Incubation of Aβ 1-42 with 11.5 (black currant extract with 25% anthocyanins caused a dose-dependent disruption disassembly/disaggregation of preformed Aβ 1-42 fibrils. It was also observed that the percent disintegration was significantly greater with 11.5 as compared to 11.4 (black currant extract with 15% anthocyanins).

In the second set of studies, the following compositions were tested:

| Composition No | Components |
|---|---|
| 18.1 | Oolong tea extract (MemorTea ®) + *Uncaria tomentosa* extract (PTI-00703 ®) (1:1) |
| 18.2 | Granulated *Uncaria tomentosa* extract (PTI-00703 ®) with acacia gum; Vitaquest, West Caldwell, NJ) |
| 18.3 | Black currant (*Ribes Nigrum*) extract powder with 15% anthocyanins (Vitaquest, West Caldwell, NJ). |
| 18.4 | Black currant (*Ribes Nigrum*) extract powder (NP Nutra, Gardena, CA). |
| 18.5 | Brian Pill ™ (contains citicoline, *bacopa monnieri*, huperzine A, vinpocetine, *gingko biloba*, vitamin B12, vitamin B6, DHA complex, phosphatidylserine, tyrosine, L-theanine, vitamin B5 and vitamin B9; Leading Edge Health, Elizabethton, TN). |
| 18.6 | Forebrain ® (contains *bacopa* extract, grape (*Vitis vinifera*) extract, extended release caffeine, vincamine, toothed clubmoss and black pepper fruit extract; Force Factor LLC) |
| 18.7 | Prevagen ® (contains 10 mg apoaequorin per each capsule; Quincy Bioscience, Madison, W.I.) |

Figure 12:
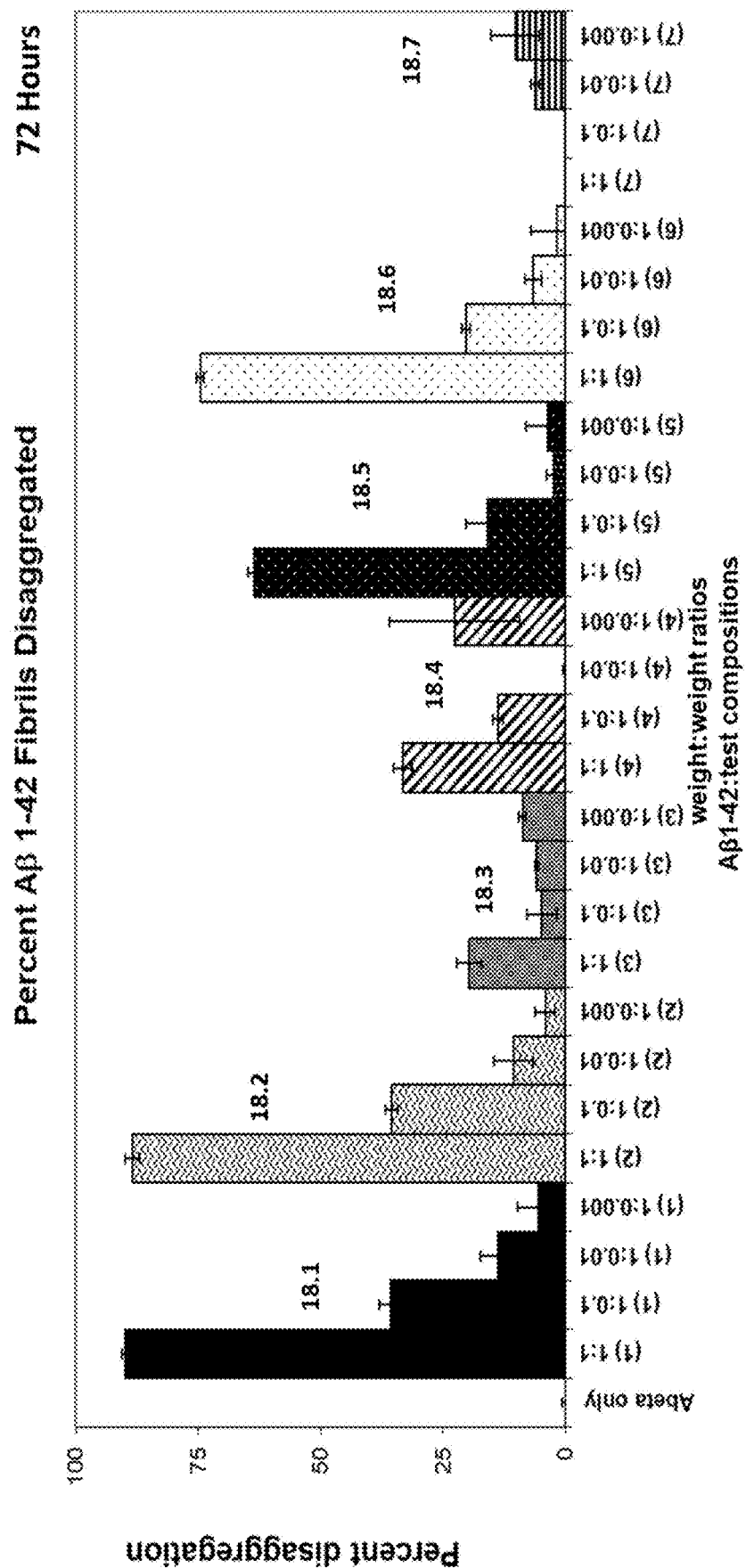
FIG. 12 depicts the graph of Aβ 1-42 aggregation measured by Thioflavin T fluorometry after incubation with: Composition 18.1; Composition 18.2; Composition 18.3; Composition 18.4, Composition 18.5, Composition 18.6, and Composition 18.7.

FIG. 12 shows the results of the 3-day incubation of with the following compositions: Composition 18.1; Composition 18.2; Composition 18.3; Composition 18.4, Composition 18.5, Composition 18.6, and Composition 18.7.

In the third set of studies, the following compositions were tested:

| Composition No | Components |
|---|---|
| 19.1 | Oolong tea extract (MemorTea ®) + *Uncaria tomentosa* extract (PTI-00703 ®) (1:1) |
| 19.2 | Granulated *Uncaria tomentosa* extract (PTI-00703 ®) with acacia gum; Vitaquest, West Caldwell, NJ) |
| 19.3 | Euro Black currant (*Ribes Nigrum*) extract powder with 25% anthocyanins (Vitaquest, West Caldwell, NJ). |
| 19.5 | Composition A |
| 19.6 | Tru Niagen ® (contains 250 mg nicotinamide riboside chloride per 2 capsules; ChromaDex, Inc., Irvine, CA) |
| 19.7 | *Uncaria tomentosa* extract (PTI-00703 ®) + Tru Niagen ® (1:1) |
| 19.8 | *Uncaria tomentosa* extract (PTI-00703 ®) + Tru Niagen ® (1:0.25) |
| 19.9 | Prevagen ® (contains 10 mg apoaequorin per each capsule; Quincy Bioscience, Madison, W.I.) |

Figure 13:
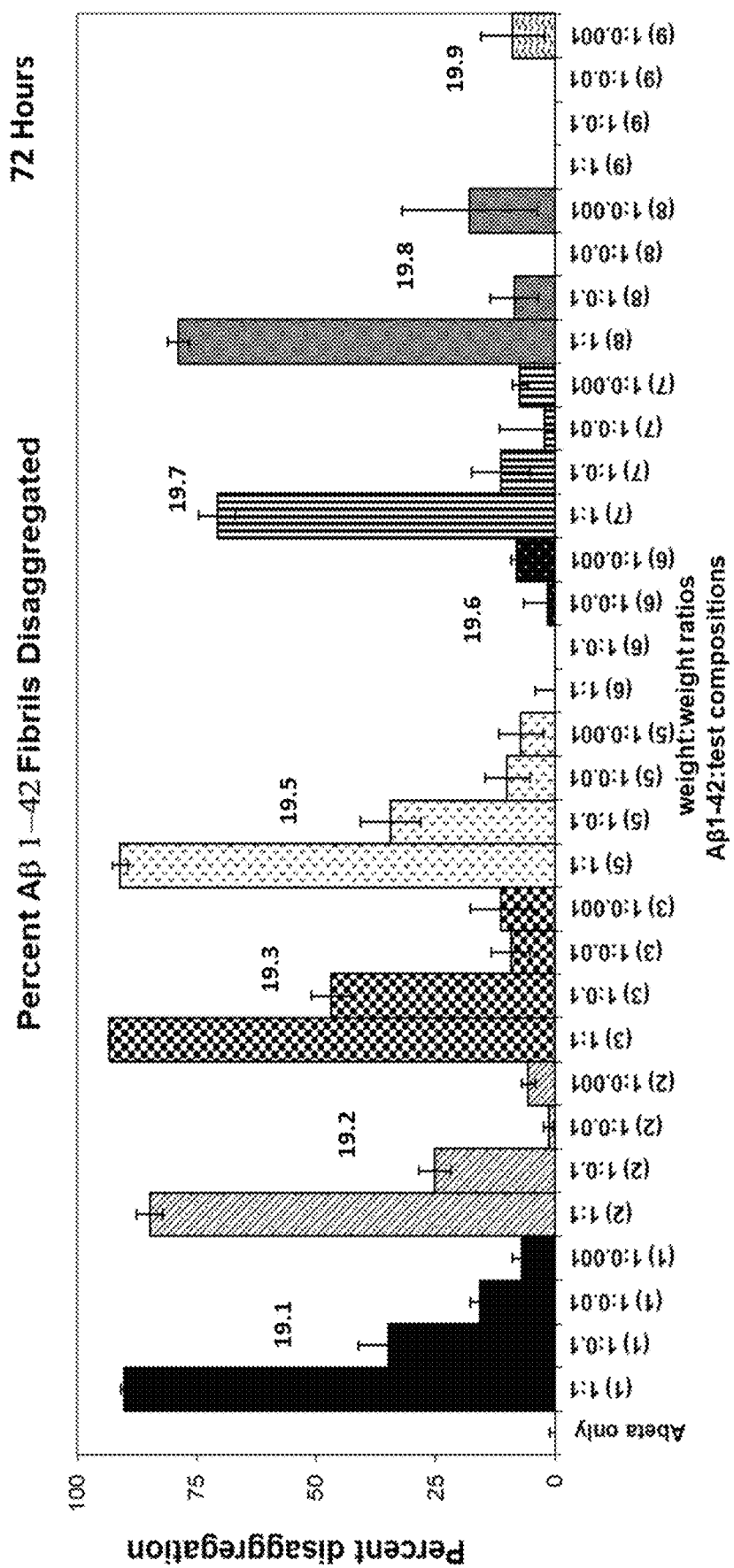
FIG. 13 depicts the graph of Aβ 1-42 aggregation measured by Thioflavin T fluorometry after incubation with: Composition 19.1; Composition 19.2; Composition 19.3; Composition 19.5, Composition 19.6, Composition 19.7, Composition 19.8, and Composition 19.9.

FIG. 13 shows the results of the 3-day incubation of with the following compositions: Composition 19.1; Composition 19.2; Composition 19.3; Composition 19.5, Composition 19.6, Composition 19.7, Composition 19.8, and Composition 19.9.

In the fourth set of studies, the following compositions were tested:

| Composition No | Components |
|---|---|
| 21.1 | Oolong tea extract (MemorTea ®) + *Uncaria tomentosa* extract (PTI-00703 ®) (1:1) |
| 21.2 | Granulated *Uncaria tomentosa* extract (PTI-00703 ®) with acacia gum; Vitaquest, West Caldwell, NJ) |
| 21.3 | Euro Black currant (*Ribes Nigrum*) extract powder with 25% anthocyanins (Vitaquest, West Caldwell, NJ). |
| 21.5 | Composition A |
| 21.6 | Oolong tea extract (MemorTea ®) + *Uncaria tomentosa* extract (PTI-00703 ®) (1:1) (Makers Nutrition, Hauppauge, NY) |
| 21.7 | Prevagen ® (contains 10 mg apoaequorin per each capsule; Quincy Bioscience, Madison, W.I.) |

Figure 14:
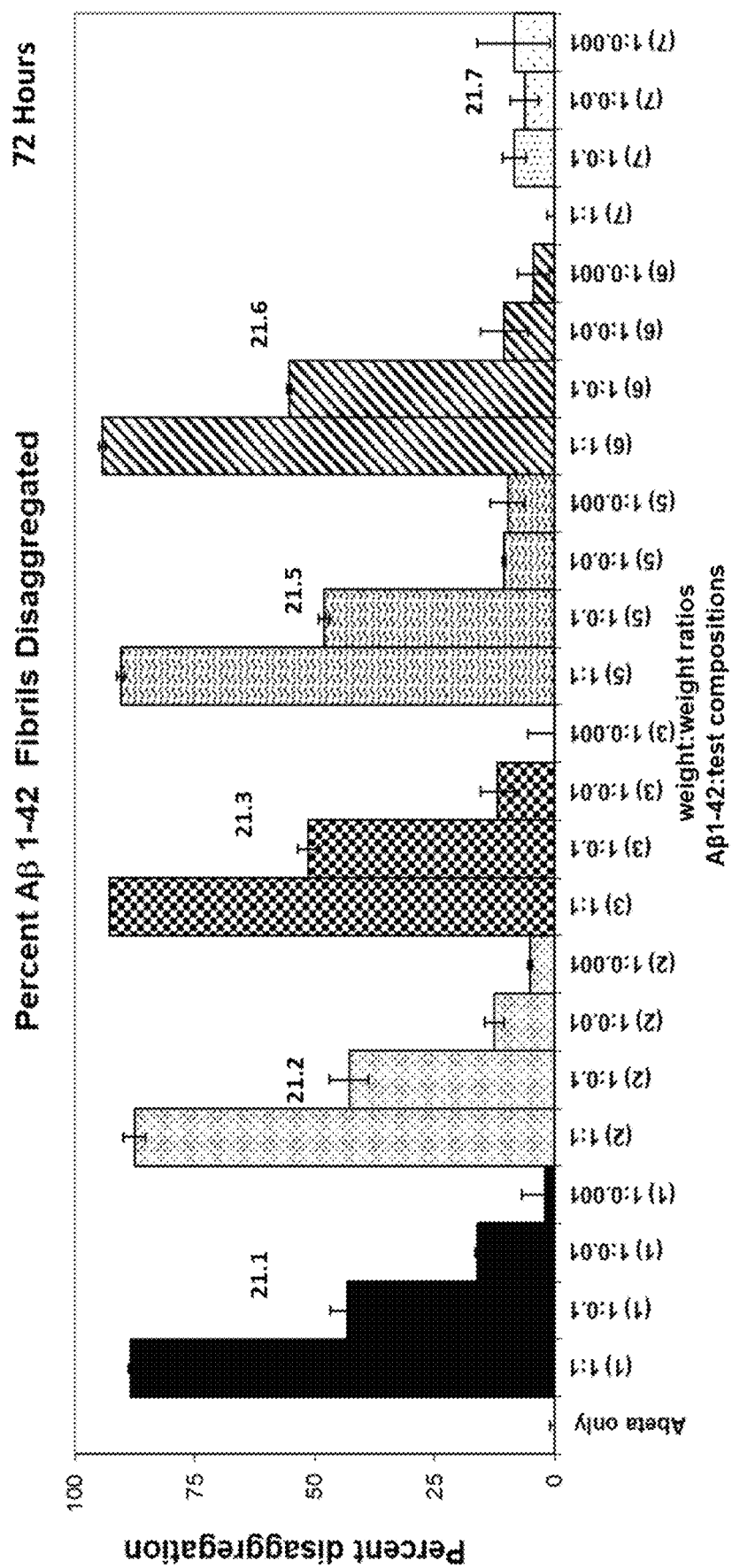
FIG. 14 depicts the graph of Aβ 1-42 aggregation measured by Thioflavin T fluorometry after incubation with: Composition 21.1; Composition 21.2; Composition 21.3; Composition 21.5, Composition 21.6, and Composition 21.7.

FIG. 14 shows the results of the 3-day incubation of with the following compositions: Composition 21.1; Composition 21.2; Composition 21.3; Composition 21.5, Composition 21.6, and Composition 21.7. These results showed that the Composition A, which is combination of black currant extract, oolong tea extract, and cat's claw extract, is a potent disruptor/inhibitor of Alzheimer's disease type A$\beta$ fibrils, and exerted its effect in a dose-dependent manner.

In another study for the combination of oolong tea extract and cat's claw extract, 40 µl of a 1 mg/ml solution (in distilled water) or pre-fibrillized human A$\beta$ 1-42 (rPeptide) was incubated at 37° C. for 3 days either alone (control), or in the presence of LOTE+PTI-00703® (at test composition: A$\beta$ weight ratios of 1:1 and 1:0.1) (referred to as "Cognitive Clarity™"). The final concentration of A$\beta$ in the reaction was 0.4 mg/ml (88 µM) in phosphate-buffered saline (PBS), pH 7.4+0.02% sodium azide in 100 µl final volume. Following 3-days of co-incubation, 12.5 µl of each incubation mixture was transferred into a 96-well microtiter plate containing 37.5 µl of PBS and 200 µl of a Thioflavin T solution (i.e. 125 µM Thioflavin T in 62.5 mM phosphate buffer, pH 6.8). The emission fluorescence was read at 485 nm (444 nm excitation wavelength) using an ELISA plate fluorometer after subtraction with buffer alone or composition alone, as blank.

For the combination of oolong tea extract and cat's claw extract, the results of the 3-day incubations are presented in FIG. 1. Incubation of A$\beta$ 1-42 with "Cognitive Clarity" (i.e. combination of LOTE+PTI-00703®) caused a dose-dependent disruption disassembly/disaggregation of preformed A$\beta$ 1-42 fibrils. At a test composition:A$\beta$ weight ratio of 0.1:1 LOTE+PTI-00703 inhibited fibrils 62.8%. At equal weight equivalents (test composition:A$\beta$ weight ratio of 1:1) there was a 93.6% inhibition of Thioflavin T fluorescence. This study showed that the combination of oolong tea extract and cat's claw extract is a potent disruptor/inhibitor of Alzheimer's disease type A$\beta$ fibrils, and exerted its effect in a dose-dependent manner.

Part B: Congo Red

In the Congo red binding assay, the ability of a test composition to alter $\beta$-amyloid binding to Congo red is quantified. In this assay, A$\beta$ 1-42 (as prepared for the Thioflavin T assay) is incubated for 3 days either alone (control), or with increasing amounts of the test compositions and then vacuum filtered through a 0.2 µm filter. The amount of A$\beta$1-42 retained in the filter is then quantitated following staining of the filter with Congo red (125 µM Congo red, 100 mM Tris, 50 mM NaCl, pH 7). After appropriate washing of the filter, any lowering of the Congo red color on the filter in the presence of the test composition (compared to the Congo red staining of the amyloid protein in the absence of the test composition) is indicative of the test composition's ability to diminish/alter the amount of aggregated and congophilic A$\beta$. It is expected that Composition A, which is combination of black currant extract, oolong tea extract, and cat's claw extract, will inhibit A$\beta$ binding to Congo red.

For the combination of oolong tea extract and cat's claw extract, the ability of Aβ fibrils to bind Congo red in the absence or presence of increasing amounts of LOTE+PTI-00703® (at test composition:Aβ weight ratios of 1:1, and 0.1:1) was determined. The results of 3-day incubations are presented in FIG. 1. LOTE+PTI-00703® caused a dose-dependent inhibition of Aβ binding to Congo red. At a test composition:Aβ weight ratio of 0.1:1, LOTE+PTI-00703® inhibited Congo red binding 20.9% ($p<0.001$). At equal weight equivalents (test composition:Aβ weight ratio of 1:1) there was a 58.6% ($p<0.001$) inhibition of Congo red binding.

Similar to the results for the Congo red binding assay, this study also indicated that this combination of a specific lead oolong tea extract (LOTE) and PTI-00703® are potent disruptors/inhibitors of Aβ fibrils as assessed by a Thioflavin T fluorometry assay, and exerted its effects in a dose-dependent manner (FIG. 1). The combination of LOTE+PTI-00703® caused a dose dependent reduction of Thioflavin T binding (indicating disruption/reduction of Aβ fibrils) by 70% ($p<0.001$) at a test composition: Aβ weight ratio of 0.1:1 (FIG. 1), and by 95% at a test composition:Aβ weight ratio of 1:1 (FIG. 1).

Part C: Slide-Based Congo Red Binding, Thioflavin S and Electron Microscopy

In the slide-based Congo red assay, Congo red dye is incubated with Aβ1-42, dotted on a slide and imaged under polarized light. Amyloid fibrils bound by Congo red emits a characteristic "apple-green birefringence" under polarized light. In this study, pre-fibrillarized 0.4 mg/ml Aβ1-42 (as prepared for the Thioflavin T assay) with or without test compositions is incubated for 3 days. 10 µl Congo red solution (250 mg Congo red dye (54% pure; Sigma) dissolved in 1 L dH20) is added to 10 µl of Aβ 1-42-/+test compositions and is mixed by vortexing for 30 seconds. Samples are incubated 10 minutes at room temperature with Congo red solution. Samples are then centrifuged at 2000 g for 3 minutes and 10 µl of supernatant is removed. 2 µl glycerol is added to the pellet and is mixed by pipetting up and down 15 times. Sample is vortexed then 10 µl of stained protein is dotted onto 18-well 5MM HTC® autoclavable blue slides. Samples are covered with small circular coverslips and then immediately imaged under polarized light. Images are captured with a Zeiss Axioscope 2 Plus microscope with HBO 100 illuminator equipped with a Q-Imaging Retiga 1300 digital camera. It is expected that Composition A, which is combination of black currant extract, oolong tea extract, and cat's claw extract, will reduce and disaggregate/dissolve pre-formed Aβ 1-42 pre-formed fibrils.

For the combination of oolong tea extract and cat's claw extract, FIG. 2A (left panel), a representative image shows that untreated A131-42 has characteristic apple-green birefringence and abundant fibrillar protein uniformly distributed across the viewing field. In FIG. 2A (right panel) treatment with LOTE+PTI-00703 (0.1:1 weight ratio with Aβ42) resulted in substantially less Congo red stained fibrils, demonstrating that the plant extract combination can reduce and disaggregate/dissolve pre-formed Aβ 1-42 pre-formed fibrils.

Similar to Thioflavin T, Thioflavin S is a related anionic dye that binds to fibrillar amyloid proteins and can be used to detect fibrillar proteins bound to a glass microscope slide. In this study, pre-fibrillarized Aβ 1-42 (as prepared for the Thioflavin T assay) with or without test compositions is incubated for 3 days. 4 µl of 0.4 mg/nil Aβ 1-42-/+test compositions are dotted onto 18-well 5MM HTC(R) autoclavable blue slides. Samples are allowed to air dry for 2 h.

10 µl of Thioflavin S solution (31 mg of Thioflavin S dissolved in 50 mL dH20) is gently applied to dried protein on slides. Protein is stained for 1 minute, then Thioflavin solution is removed by pipette. 40 µl of a 70% ethanol solution is gently pipetted onto stained protein for 1 minute to rinse. This solution is gently removed by pipette. 2 µl of Vectashield (Vector) mounting media is applied to the stained protein and then covered with circular coverslips. Images are viewed under fluorescent light and images are captured with a Zeiss Axioscope 2 Plus microscope with HBO 100 illuminator equipped with a Q-Imaging Retiga 1300 digital camera. It is expected that Composition A, which is combination of black currant extract, oolong tea extract, and cat's claw extract, will substantially reduce Thioflavin S fluorescent fibrils.

Figure 2B:
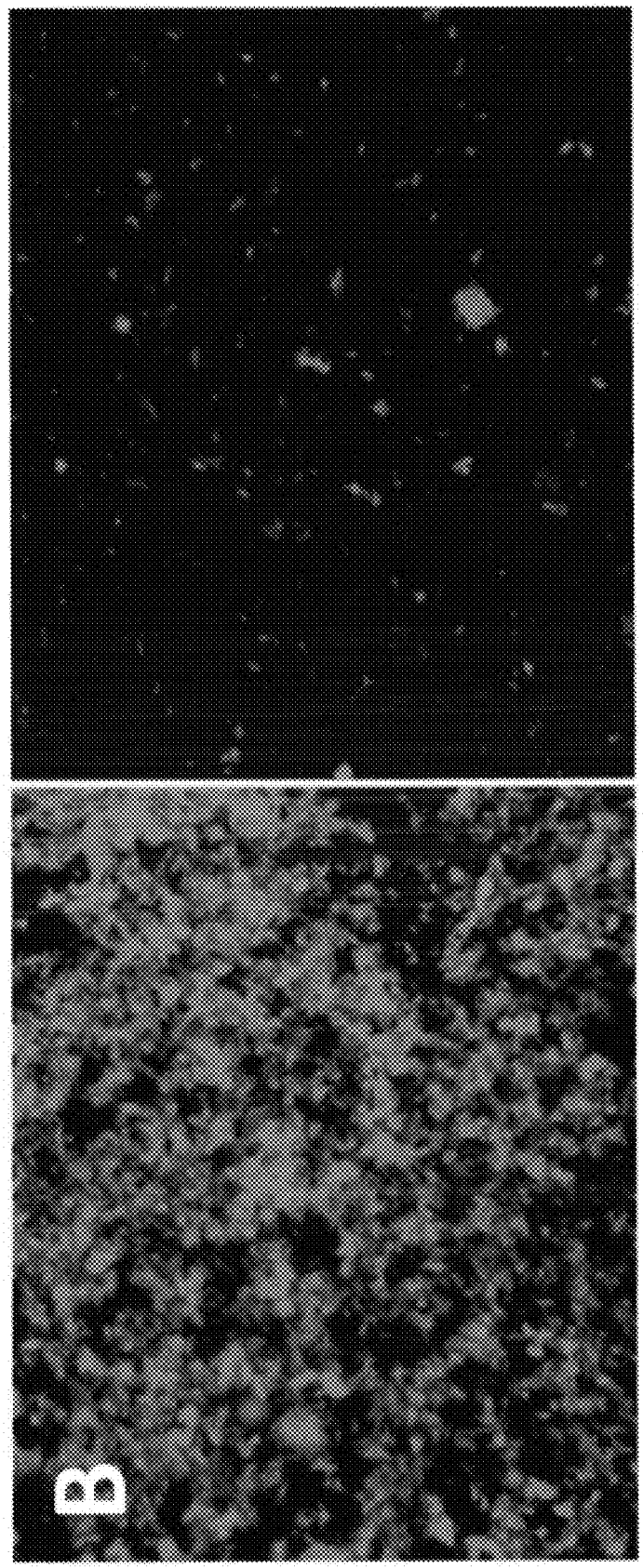

For the combination of oolong tea extract and cat's claw extract, FIG. 2B (left panel), a representative image of untreated Aβ 1-42 shows abundant Thioflavin S fluorescent fibrils uniformly distributed across the viewing field. Pre-formed Aβ 1-42 fibrils incubated with LOTE+PTI-00703® (at 0.1:1 weight ratio with Aβ1-42) for 72 hr showed a substantial reduction in fluorescent fibrils (FIG. 2B, right panel). In FIG. 2B (right panel), representative images show that with LOTE+PTI-00703 treatment, the Thioflavin S-fluorescent fibrils disappeared.

Negative stain electron microscopy (EM) analysis is used to independently monitor the effectiveness of different compositions to disrupt pre-formed Aβ fibrils. In these experiments, pre-formed Aβ 1-42 fibrils (as prepared for the Thioflavin T assay) are incubated in the absence (control) or presence of increasing concentrations of test compositions. After the 3-day incubation, 10 µl samples are spotted onto grids, stained with 2% uranyl acetate, and visualized at 8,000× to 30,000× magnifications with a JEOL 1010 transmission electron microscope. It is expected that EM analysis will show that treatment of Composition A, which is combination of black currant extract, oolong tea extract, and cat's claw extract, will significantly reduce and will dissolve the number of clumped Aβ fibrils. It is expected that these studies will demonstrate that Composition A, which is combination of black currant extract, oolong tea extract, and cat's claw extract, is a potent Aβ disruptor/inhibitor.

Figure 2C:
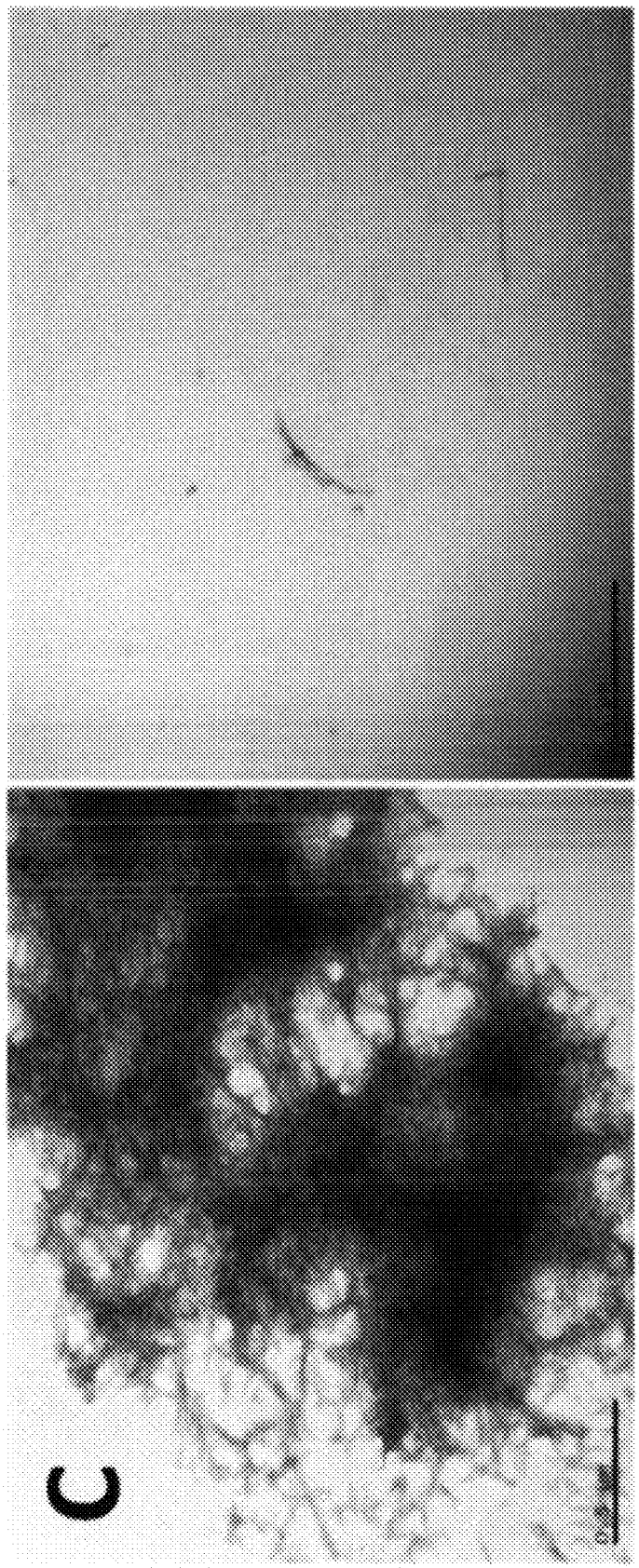

For the combination of oolong tea extract and cat's claw extract, FIG. 2C (bottom panel), EM analysis confirmed formation of Aβ fibrils in the absence of treatment (i.e. FIG. 2C, Control). Without treatment (2C, left panel), Aβ formed large clumped fibrils that uniformly covered the field. These samples were also tested by the Thioflavin T assay and confirmed to be Thioflavin T-fluorescence positive fibrils. In the presence of LOTE+PTI-00703® (FIG. 2C, right panel), the number of clumped Aβ fibrils was significantly reduced and dissolved. These results correlate well with the Thioflavin T fluorometry data that showed a reduction in Thioflavin T fluorescence with treatment and Congo red binding data that showed a reduction in Congo red binding with treatment. Using these independent methodologies, we have identified and validated the lead oolong tea extract (LOTE) in combination with PTI-00703® (i.e. LOTE+PTI-00703M as potent Aβ disruptors/inhibitors.

Example 2: Inhibition/Disruption of the In Vitro Conversion of Aβ to β-Sheet Containing Fibril Structures Part A: Thioflavin T Fluorometry To test whether the compositions described herein, can inhibit the β-sheet formation of Aβ, the same Thioflavin T assay as described in Example 1 is utilized, but with Aβ 1-40 as a substrate instead. Similar to Aβ 1-42, Aβ 1-40 forms Thioflavin T positive aggregates but requires >24 h incubation at 37° C. shaking to become fully fibrillarized. Since Aβ 1-40 is in a non-fibrillar state at the start of the assay, this protein can be aggregated in the presence of compositions to measure aggregation inhibition. Lyophilized human Aβ 1-40 (rPeptide) is dissolved to 1 mg/mL (220 μM) in dH20. In separate test tubes, test composition stocks are prepared in PBS at various concentrations such that final reactions containing equal volumes of the test composition stocks and the Aβ solution would result in a final Aβ concentration of 0.5 mg/mL (110 μM) with test composition:Aβ weight ratios of 1:1, 0.5:1, 1:1, and 0.2:1. The reactions containing Aβ+test compositions (or Aβ+PBS as a control for Aβ aggregation) are then incubated for 2 days. The incubation mixtures are diluted 1:10 to 0.05 mg/ml. Aft and 50 μL of each diluted incubation mixture are transferred into a 96-well microtiter plate containing 200 μL of Thioflavin T solution (i.e. 125 μM Thioflavin T in 62.5 mM phosphate buffer, pH 6.8). The fluorescence is read at 485 nm (444 nm excitation wavelength) using an ELISA plate fluorometer after subtraction with PBS buffer alone or composition alone, as blank. It is expected that Composition A, which is combination of black currant extract, oolong tea extract, and cat's claw extract, will inhibit the β-sheet formation of Aβ. Specifically, it is expected that this study will show that Composition A is a potent inhibitor of β-sheet rich-Aβ fibril formation as assessed by Thioflavin T fluorometry, and may exert its effect in a dose-dependent manner.

Figure 3:
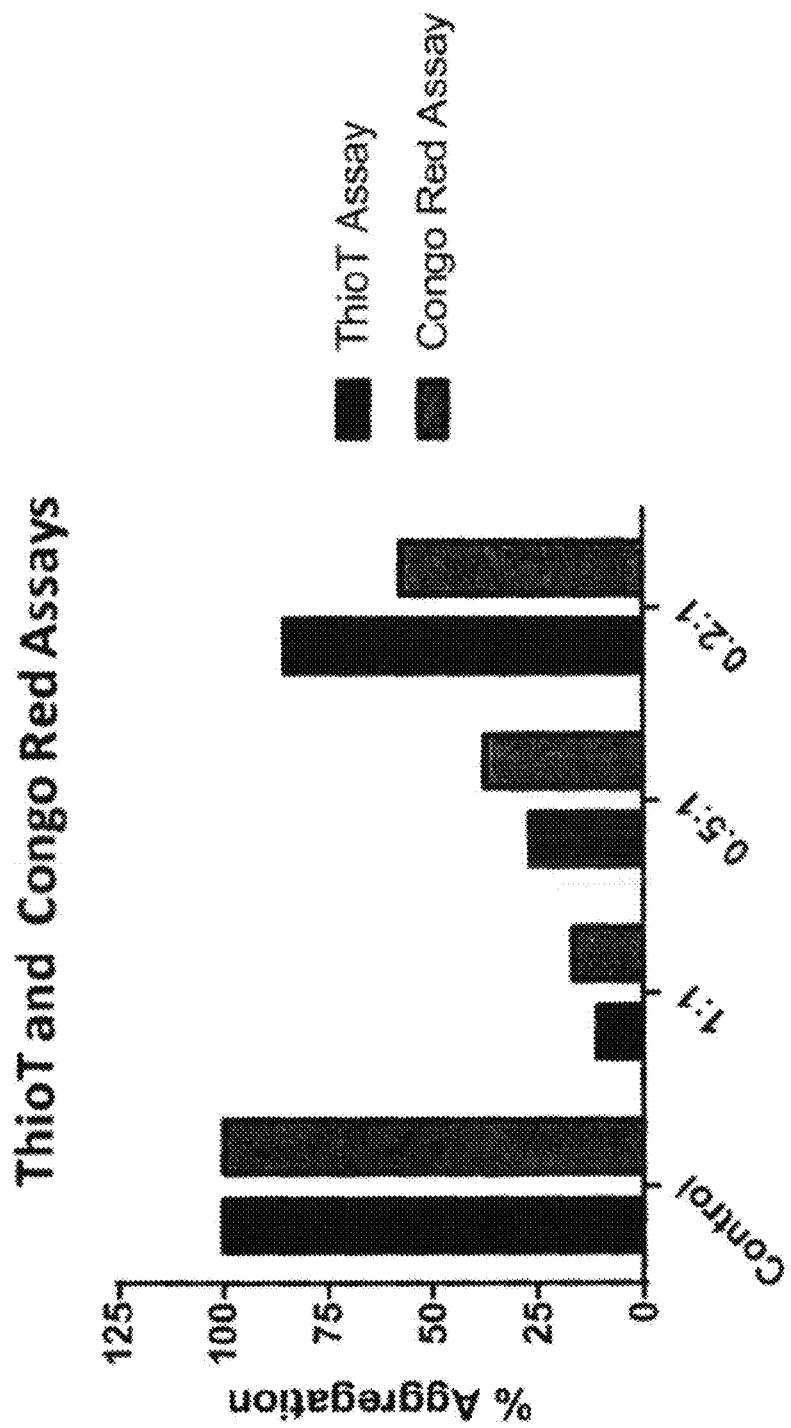
FIG. 3 depicts a graph of Aβ 1-40 aggregation measured by Thioflavin T fluorometry and Congo red binding after incubation with LOTE and PTI-00703®.

For the combination of oolong tea extract and cat's claw extract, the LOTE+PTI-00703® was evaluated in another study. The results of this study presented in FIG. 3 indicated that LOTE+PTI-00703® of this invention interfered with Aβ aggregation as indicated by its ability to prevent the formation of fibrils as assessed by Thioflavin T fluorometry. At a test composition:Aβ weight ratio of 0.2:1 LOTE+PTI-00703® inhibited fibrils by 14.1% and at 0.5:1 LOTE+PTI-00703® inhibited fibrils at 73% (p<0.001). At equal weight equivalents (test composition:Aβ weight ratio of 1:1) there was an 89.3% inhibition (p<0.001) of Thioflavin T fluorescence. This study indicated that LOTE+PTI-00703® is a potent inhibitor of β-sheet rich-Aβ fibril formation as assessed by Thioflavin T fluorometry, and this combination exerts its effect in a dose-dependent manner.

Part B: Congo Red

To test whether the compositions described herein can inhibit β-sheet formation of AP, the same Congo red assay as described in Example 1 is utilized, but with Aβ 1-40 as a substrate instead. In this assay, Aβ 1-40 (as prepared for the Thio T assay) and test compositions are incubated for 2 days and then vacuum filtered through a 0.2 μm filter. The amount of Aβ 1-40 retained in the filter is then quantitated following staining of the filter with Congo red (125 μM Congo red, 100 mM Tris, 50 mM NaCl, pH 7). After appropriate washing of the filter, any lowering of the Congo red color on the filter in the presence of the test composition (compared to the Congo red staining of the amyloid protein in the absence of the test composition) is indicative of the test composition's ability to diminish/alter the amount of aggregated and congophilic Aβ. It is expected that Composition A, which is combination of black currant extract, oolong tea extract, and cat's claw extract, will inhibit the β-sheet formation of Aβ. Specifically, it is expected that this study will show that Composition A is a potent inhibitor of Aβ fibrils as assessed by Aβ fibril binding to Congo red, and may exert its effect in a dose-dependent manner.

For the combination of oolong tea extract and cat's claw extract, the ability of Aβ fibrils to bind Congo red in the absence or presence of increasing amounts of LOTE+PTI-00703® (at test composition:Aβ weight ratios of 1:1, 0.5:1, and 0.2:1) was determined in another study. The results of 2-day incubations are presented in FIG. 3. LOTE+PTI-00703® caused a dose-dependent inhibition of Aβ binding to Congo red. At a test composition:Aβ weight ratio of 0.2:1 LOTE+PTI-00703 inhibited Congo red binding 41.7% and 0.5:1 LOTE+PTI-00703® inhibited Congo Red binding 62.5% (p<0.001). At equal weight equivalents (test composition:Aβ weight ratio of 1:1) there was an 83.3% inhibition (p<0.001) of Congo red binding. Similar to the results for the Thioflavin T fluorometry assay, this study also indicated that LOTE+PTI-00703® is a potent inhibitor of Aβ fibrils as assessed by Aβ fibril binding to Congo red, and exerts its effect in a dose-dependent manner.

Part C: CD Spectroscopy

CD spectroscopy is performed to determine the potency of the compositions described herein to inhibit formation of Aβ 1-40 β-sheet secondary structure under aggregation-prone conditions. Since β-sheet structure is characteristic of Aβ fibrils, monitoring secondary structure of protein can provide additional proof of a compositions' effectiveness at inhibiting aggregation. CD spectra of Aβ 1-40 samples with increasing −/+ concentrations of compositions are analyzed at 25° C. on a JASCO Model J-810 Spectropolarimeter. CD spectroscopy and ThioT assays are analyzed in parallel from the same sample preparation in order to correlate the results from two independent assays. It is expected that CD spectra analysis will show that Composition A, which is combination of black currant extract, oolong tea extract, and cat's claw extract, will significantly inhibit abnormal assembly of Aβ into fibrillar, β-sheet assemblies and will maintain Aβ 1-4) in a less pathogenic form.

Figure 4:
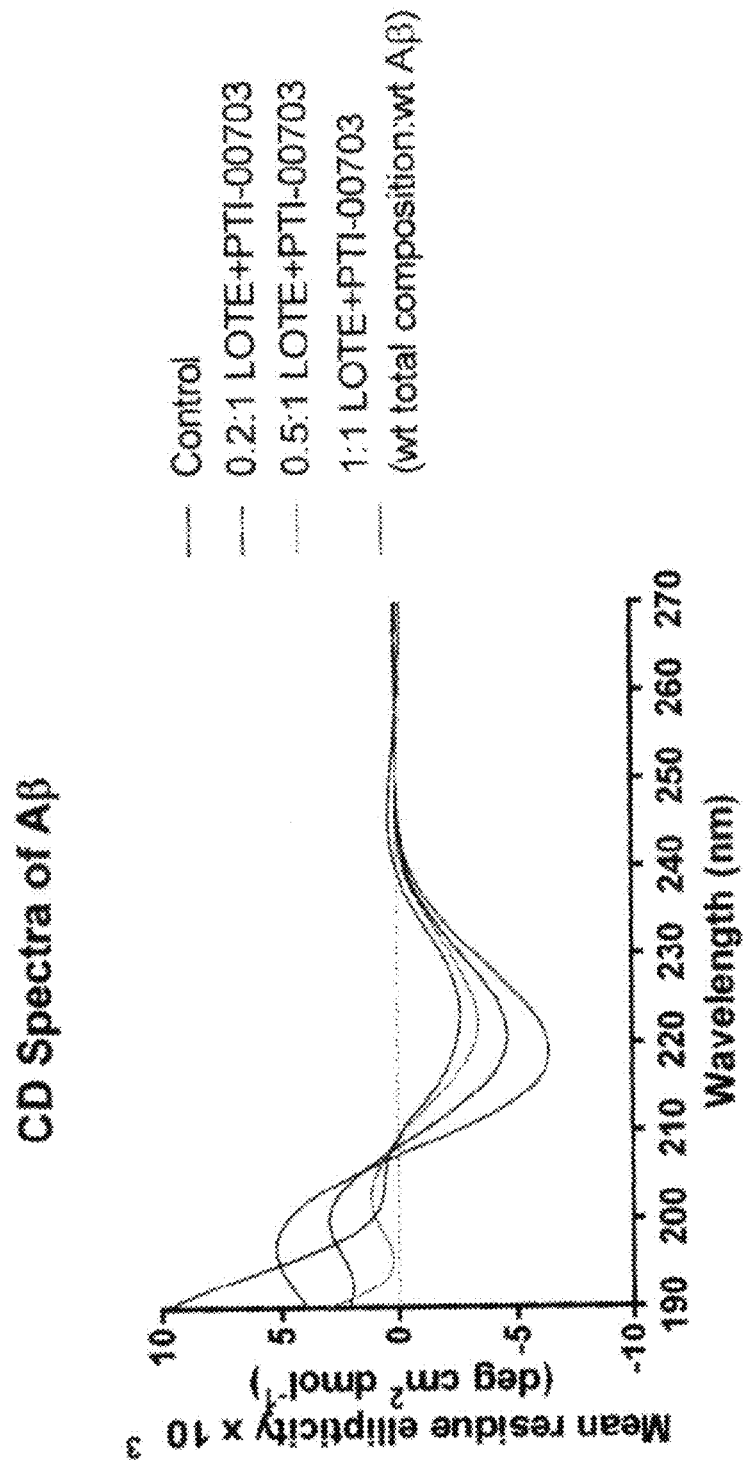
FIG. 4 depicts a circular dichroism spectra of Aβ 1-40 after treatment with increasing concentrations of LOTE and PTI-00703®.

For the combination of oolong tea extract and cat's claw extract, CD spectra of Aβ 1-40 treated with LOTE+PTI-00703® was performed. In FIG. 4, the CD spectra of Aβ 1-40 treated with LOTE+PTI-00703® indicated a dose-dependent inhibition of β-sheet containing fibrils. A minima at 218 nm indicates the presence of β-sheet structure. A positive shift of ellipticity at 218 nm indicates less β-sheet structure. At a test composition:Aβ weight ratio of 0.2:1 LOTE+PTI-00703® demonstrated 30.9% less β-sheet structure from untreated, 0.5:1 LOTE+PTI-00703® showed 53.9% less β-sheet structure than control. At equal weight equivalents (test composition:Aβ weight ratio of 1:1) there was 64.8% less β-sheet structure compared to control. These data verified LOTE+PTI-00703® has a significant ability to inhibit abnormal assembly of Aβ into fibrillar, β-sheet assemblies and maintains Aβ 1-40 in a less pathogenic form.

Example 3: Use of Recombinant Tau Repeat Domain for In Vitro Screening of Tau Aggregation Inhibitors In previous studies relating to in vitro screening for identification of tau aggregation inhibitors, the present Inventors found that under the same experimental conditions, formation of paired helical filaments (PRFs) from commercially-purchased full-length tau protein (Tau441; from rPeptide) was much slower (>11 days; data not shown) than that from the tau repeat domain (TauRD; containing Q244-E372 of Tau441) (≥24 hr) (S. Barghorn et al, *Methods Mol Biol*, 299: 35-51, 2005).

Because of the remarkably short turn-around time and common aggregation properties, TauRD was used for in vitro screening for tau aggregation inhibitors. Since the TauRD protein was not commercially available, TauRD was prepared in accordance to the following procedure, which is also described in US 2016/0250273, which is incorporated by reference for the disclosure of this procedure. A cDNA fragment coding for the human TauRD was cloned into a bacterial expression vector and the construct was then expressed in *E. coli*. Bacterial clones demonstrating high levels of expression of TauRD were then selected for protein purification. The recombinant TauRD protein was then purified by heat-stability treatment and cation exchange chromatography as described with minor modifications (S. Barghorn et al, Methods Mol Biol, 299: 35-51, 2005). Using this method, a protein yield of 20 mg per liter of bacterial culture was obtained. Aggregation and PHF formation of purified TauRD were evaluated and validated by independent assays including Thioflavin S (ThioS) fluorometry, a dye that fluoresces after binding to fibrils, circular dichroism (CD) spectroscopy, a method that detects changes in secondary structure of proteins and electron microscopy. The results consistently demonstrate that TauRD (10 μM) is able to form ThioS-positive, β-sheet-containing PHFs when incubated with equimolar heparin (Sigma-Aldrich, St. Louis, Mo.) at 37° C., with shaking at 800-1000 rpm for ≥1 day.

In FIG. 5A, TauRD (15 kDa) protein was purified from *E. coli* and evaluated by SDS-PAGE/silver stain with typical purity of >95%. CD spectroscopy was used to evaluate the non-aggregated and aggregated TauRD proteins, and FIG. 5B-C are examples of CD spectroscopy of non-aggregated and aggregated TauRD proteins. TauRD aggregates were prepared in the presence of equimolar (10 μM) ratios of TauRD and heparin in 20 mM sodium phosphate buffer (pH7.4), incubated at 37° C. with shaking for 0-120 h. In the absence of heparin, CD spectra of non-aggregated TauRD was random coil with ellipticity minima at 195 nm (FIG. 5B). In the presence of heparin, CD spectra showed time-dependent conformational changes of TauRD protein from random coil (minima at 195 nm) at time 0 to β-sheet (minima at 218 nm) at 20-120 h (FIG. 5C). TauRD aggregation was monitored by ThioS fluorometry over time (FIG. 5D). The results show formation of ThioS-positive TauRD fibrils after 20 h incubation. In the absence of heparin without fibril formation, tauRD ThioS signals were <200 arbitrary units (A.U.) of fluorescence at all time points. Tau fibril formation was confirmed by negative stain EM (FIG. 5E-G), which showed formation of Tau fibrils after 48 h incubation with heparin. TauRD monomers at time 0 are shown in FIG. 5E (Bar=200 nm). Formation of TauRD fibrils at 48 hr are shown in FIGS. 5F-G (Bar=50 nm). Both straight and paired helical filaments were found.

Example 4: Identification of Novel Tau Aggregation Inhibitors by Thioflavin S Fluorometry Screening A well-known method for measuring fibril formation is Thioflavin T (ThioT) fluorometry (H. Naiki et al, Lab. Invest. 65:104-110, 1991; H. Levine III, *Protein Sci.* 2:404-410, 1993; H. Levine III, *Amyloid* 2:1-6, 1995; H. Naiki and K. Nakakuki, *Lab. Invest.* 74:374-383, 1996). ThioT is known to bind to fibrillar proteins, and an increase in fluorescence correlates with an increase in fibril formation, whereas a decrease in fluorescence correlates with a decrease in fibrils due to disassembly and/or disruption. The assay is modified by replacing ThioT with Thioflavin S (ThioS), a related anionic dye with similar properties, because the latter has been shown to be more sensitive, and reproducible for quantifying Tau PHFs (data not shown; P. Friedhoff et al, Biochemistry, 37(28): 10223-30, 1998). ThioS fluorometry is employed to assess whether the above described compositions are capable of causing a disassembly/disruption of fibrils.

Aggregated tau fibrils are prepared in the presence of equimolar ratios of TauRD and heparin (10 μM each) in 20 mM sodium phosphate buffer, pH7.4. The reaction mixture is incubated at 37° C. with shaking (800-1000 rpm) for 24 h to 72 h. Test compositions are tested at varying weight to weight concentrations with 0.14 mg/ml TauRD with heparin. The same reaction mixtures (+increasing concentrations of test compositions) but without TauRD are also set up in parallel to serve as background controls.

Following 24-72 h of co-incubation, 50 μl of each incubation mixture is transferred into a black 96-well microtiter plate (Santa Cruz Biotechnology, Inc., Dallas, Tex.) with 50 μl of phosphate buffered saline (PBS; Sigma-Aldrich, St. Louis, Mo.) and 25 μl of Thioflavin S solution (500 mM Thioflavin S; Sigma-Aldrich, St. Louis, Mo. in PBS, pH 7.4). Using an ELISA plate fluorometer, fluorescence is read at 485 nm (444 nm excitation wavelength) after subtraction with buffer alone or composition alone, as blank.

Inhibition of tau aggregation by 50%, $IC_{50}$, is calculated using Prism version 5 software (GraphPad Software) by nonlinear regression [(Log [inhibitor] vs. normalized response; variable slope)]. It is expected that Composition A, which is combination of black currant extract, oolong tea extract, and cat's claw extract, will significantly reduce ThioS-positive tau aggregates. It is also expected that this study will show that Composition A is an inhibitor of tau aggregation/fibrillogenesis that could be used as a novel therapeutic for tauopathies.

Figure 6:
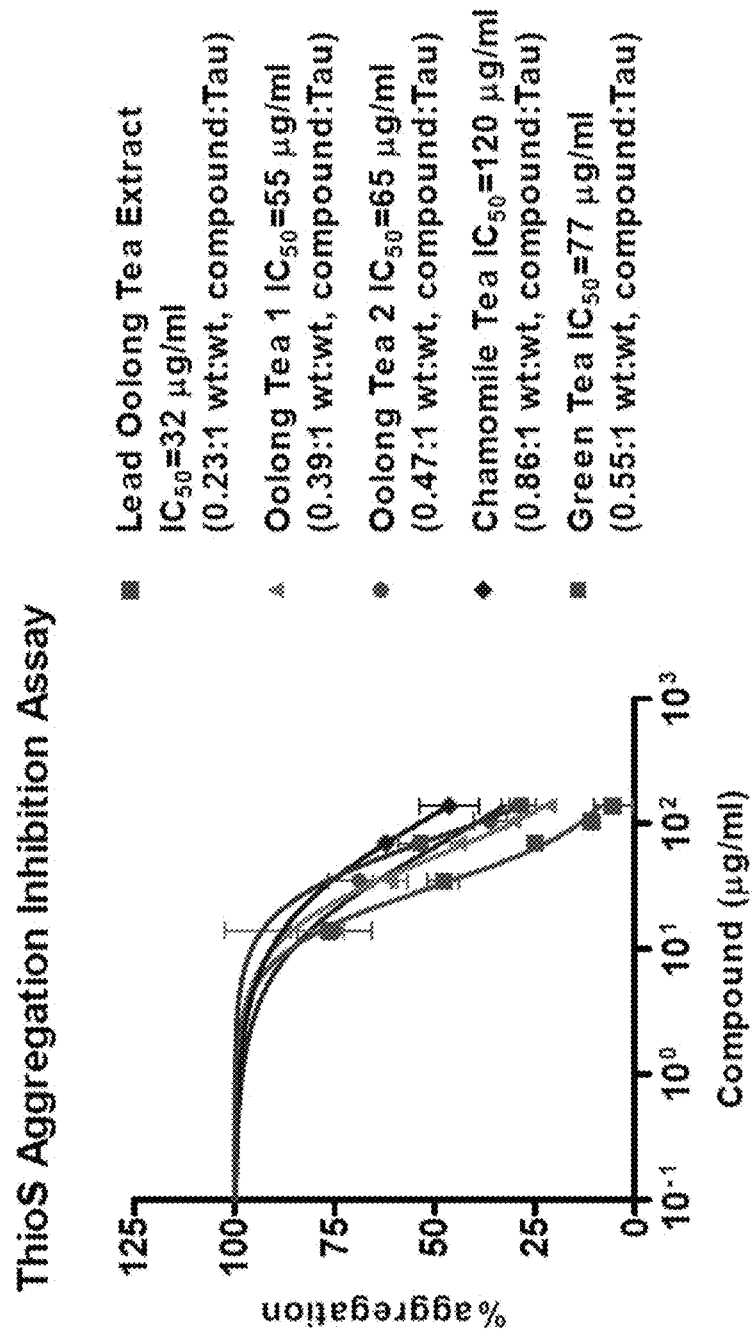
FIG. 6 depicts a graph of tau aggregation measured by Thioflavin S fluorometry after incubation with tea extracts.

In another study, over 25 tea extracts were tested for inhibition of ThioS-positive tau aggregates. A majority of teas were oolong tea extracts. FIG. 6, is an example of ThioS fluorescence of tau aggregated in the presence of a few oolong tea extracts, chamomile tea and green tea. Increasing concentrations of extracts were incubated with 0.14 mg/ml (10 μM) tauRD and equimolar heparin for 24-72 h, shaking at 1000 rpm, 37° C. The lead oolong tea extract (LOTE) inhibited tau aggregates more than other oolong teas, chamomile tea or green tea extract. LOTE inhibited tau aggregation 50% ($IC_{50}$) with a ratio of 0.23:1, weight:weight, of composition to tau. This experiment demonstrates LOTE has a superior ability over other compositions to inhibit abnormal assembly of tau into fibrillar, pathogenic assemblies.

Figure 7:
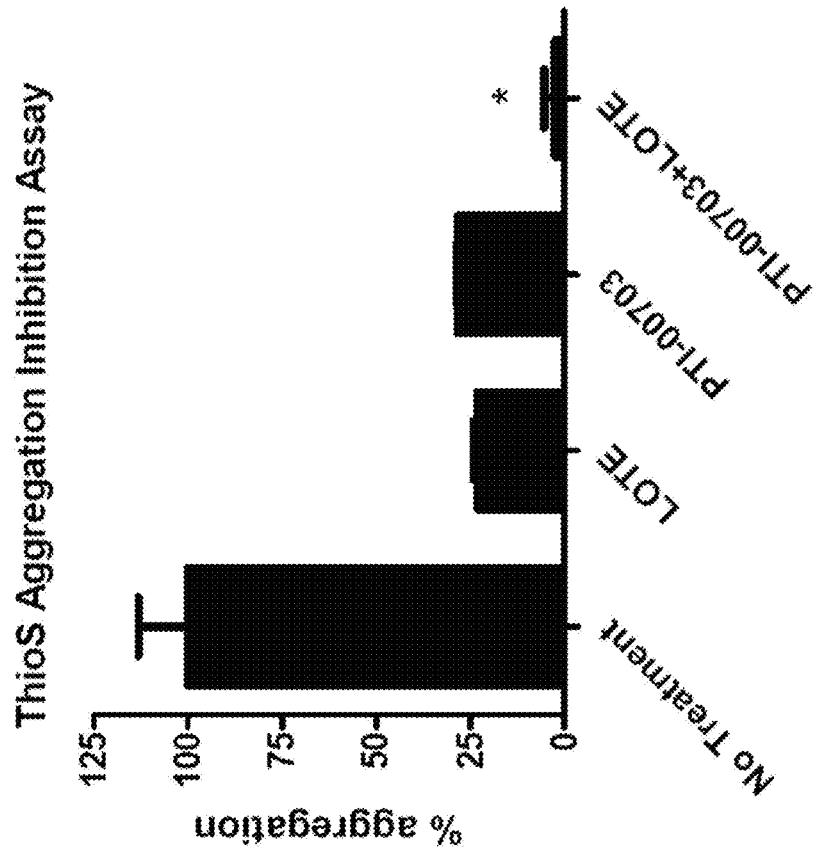
FIG. 7 depicts a graph of tau aggregation measured by Thioflavin S fluorometry after incubation with LOTE and PTI-00703®.

After identifying a tea extract that has excellent tau aggregation inhibition, lead oolong tea extract (LOTE) was incubated alone or in combination with PTI-00703® in the tau aggregation inhibition assay. A combination of specific oolong tea and PTI-00703® inhibited ThioS-positive tau aggregates more than LOTE or PTI-00703® alone (*significant by paired t-test, p<0.05) (FIG. 7). This combination of lead oolong tea extract and PTI-00703® is a potent inhibitor of tau aggregation/fibrillogenesis that could be used as a novel therapeutic for tauopathies.

Example 5: Confirmation of Tau Aggregation Inhibition by Analysis of Protein Secondary Structure by Circular Dichroism (CD) Spectroscopy CD is a powerful method that provides dye-independent confirmation that the structure of a protein has changed. CD measures the differential absorption between left and right handed circularly polarized light. Proteins contain elements of asymmetry that exhibit distinct CD signals measured in units of ellipticity. Thioflavin S fluorescent, tau aggregates have an ellipticity minima of 218 nm, which is characteristic of β-sheet containing proteins. Non-aggregated tau has an ellipticity with a characteristic minima at 195 nm indicating random coil structure. CD spectroscopy is performed to determine the potency of any one of the compositions described herein to inhibit formation of β-sheet secondary structure in TauRD under aggregation-prone conditions. CD spectra are taken from samples containing+/— TauRD with increasing concentrations of compounds, and analyzed at 25° C. on a JASCO Model J-810 Spectropolarimeter. CD spectroscopy and Thio S assays are analyzed in parallel from the same sample preparation in order to correlate the results from two independent assays. It is expected that Composition A, which is combination of black currant extract, oolong tea extract, and cat's claw extract, will inhibit abnormal assembly of tau into fibrillar, β-sheet assemblies and will maintain tau in a non-pathogenic soluble, random coil form.

Figure 8:
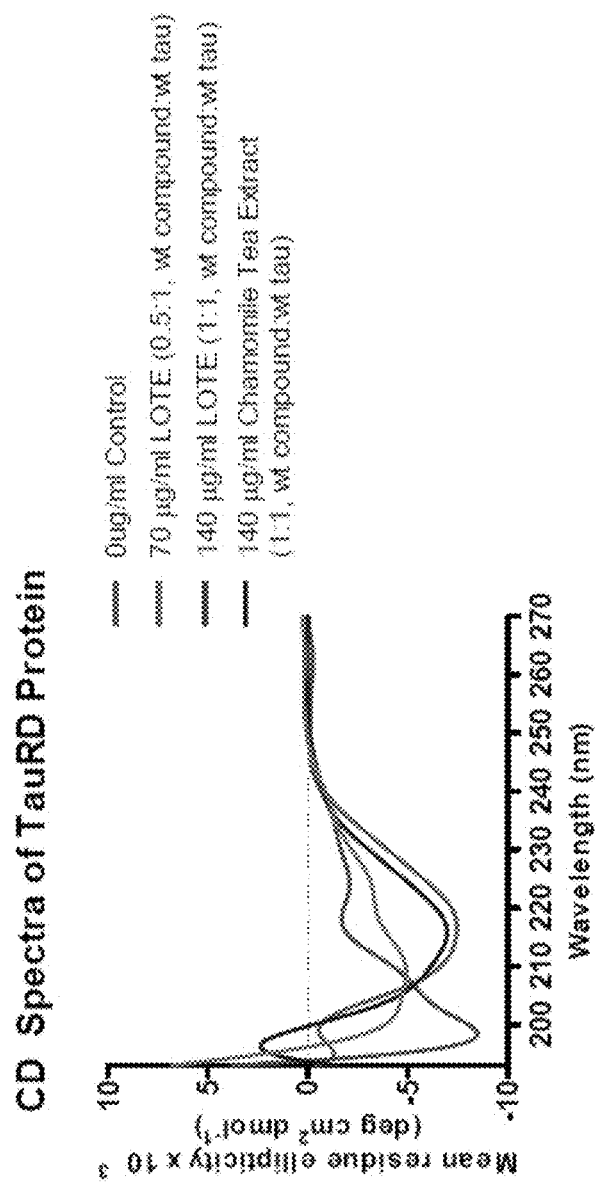
FIG. 8 depicts a graph of tau secondary structure measured by circular dichroism spectroscopy after treatment with LOTE.

In another study, the combination of oolong tea extract and cat's claw extract was evaluated. In FIG. 8, tau was treated with lead oolong tea extract (LOTE) or chamomile tea extract for 48 h. Tau treated with LOTE is dose-dependently inhibited from converting to β-sheet containing fibrils. At the highest concentration of LOTE treatment, tau remains in soluble, random coil form with a minima ~195 nm. Conversely, at the highest concentration of treatment with chamomile tea extract, tau still changes to an aggregated, β-sheet structure similar to the untreated control. These data confirm LOTE has a significant ability over other compositions to inhibit abnormal assembly of tau into fibrillar, β-sheet assemblies and maintains tau in a non-pathogenic soluble, random coil form.

Example 6: Inhibition of Tau Protein Fibrillogenesis and Disaggregation of Preformed Tau Fibrils Determined by Negative Stain Electron Microscopy (EM)

EM analysis is used to independently monitor the effectiveness of any one of the compositions described herein to inhibit tau fibrillogenesis. In these experiments, tau fibrils are assembled by incubating equimolar ratios of TauRD protein and heparin (10 µM each) in the absence (control) or presence of increasing concentrations of test compositions. After the 2-day incubation, samples are spotted onto grids, stained with 2% uranyl acetate, and visualized at 8,000× to 30,000× magnifications with a JEOL 1010 transmission electron microscope. It is expected that Composition A, which is combination of black currant extract, oolong tea extract, and cat's claw extract, will inhibit tau fibril formation with EM analyis. It is expected that the results of Composition A will correlate well with ThioS fluorometry and CD analysis, which will show a reduction in ThioS fluorescence and decrease in β-sheet structure. It is also expected that EM analysis will show that Composition A will inhibit tau aggregation and will also disaggregate preformed tau fibrils. It is expected that these studies will show Composition A is potent inhibitor of tau aggregation/fibrillogenesis.

Figure 9:
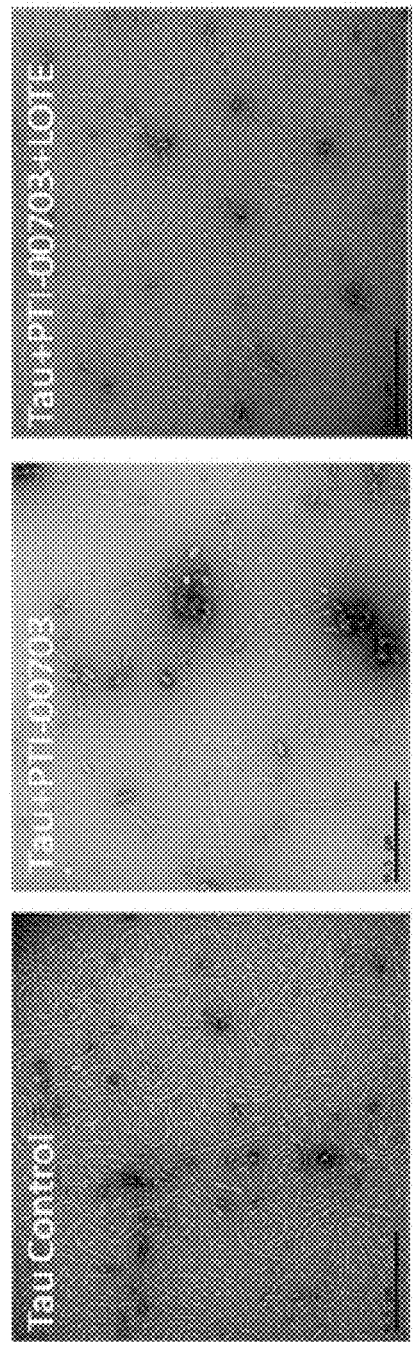
FIG. 9 depicts electron micrograph of tau fibril formation with PTI-00703® and LOTE.

In another study, for the combination of oolong tea extract and cat's claw extract, FIG. 9, left panel, EM analysis confirmed formation of tau fibrils in the absence of treatment. Without treatment, tau formed a mixture of paired straight and helical filaments similar to those found in human tauopathies (V. M. Lee et al., Ann. Rev. Neurosci. 24:1121-159, 2001). These samples were also tested by the ThioS assay and CD and confirmed to be ThioS-fluorescence positive and β-sheet in structure. In the presence of PTI-00703® and PTI-00703®+LOTE (FIG. 9, middle and right panel), tau fibrils become shortened and sparse, indicating an inhibition of tau fibril formation. Even less fibrils are apparent in tau samples treated with both PTI-00703® and LOTE. These results correlate well with ThioS fluorometry and CD analysis, which showed a reduction in ThioS fluorescence and decrease in β-sheet structure. Using three independent methodologies, we have identified and validated PTI-00703+lead oolong tea extract as a potent inhibitor of tau aggregation/fibrillogenesis.

Figure 10:
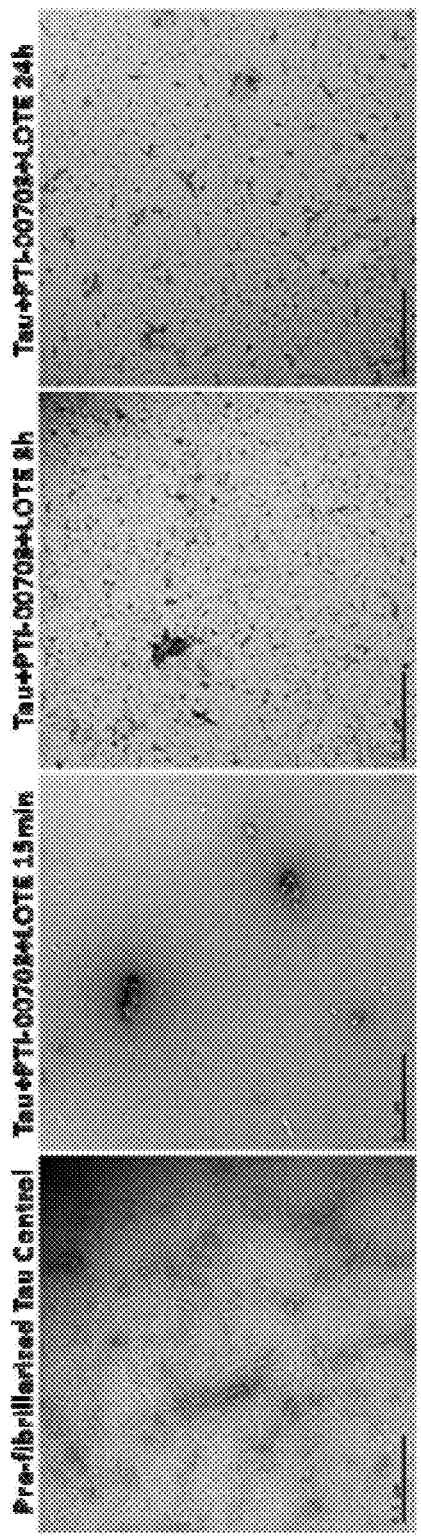
FIG. 10 depict electron micrographs of preformed tau fibrils treated with PTI-00703® and LOTE.

Utilizing EM analysis, preformed tau fibrils were shown to rapidly disaggregate in the presence of both PTI-00703® and LOTE. TauRD was incubated with equimolar heparin to form fibrils as described in the previous assay. TauRD was diluted with or without test compositions and incubated, shaking at 37° C. for various time points. At each time point tauRD+/− test compounds was assayed for ThioS fluorescence and snap frozen for EM analysis. In FIG. 10 (left panel) without treatment, pre-fibrillarized tau remained in long filaments. In the next panels, pre-fibrillarized tau was found to rapidly disaggregate in the presence of PTI-00703®+LOTE. As early as 15 minutes incubation with PTI-00703®+LOTE, tau fibrils are shorter and sparser than without treatment. Disruption of tau fibrils was also confirmed by ThioS assay (data not shown). These data indicate the composition of PTI-00703®+LOTE not only can inhibit tau aggregation but can disaggregate preformed tau fibrils.

Example 7: Dissolution of Cat's Claw/Oolong Tea Extract by the Addition of Black Currant Extract In the next example, comparisons were made between the solubility of cat's claw/oolong tea extract versus cat's claw/oolong tea extract with black currant extract added. In visual assays, one glass of water was used to observe the dissolution of cat's claw/oolong tea versus cat's claw/oolong tea with 50 mg of Euro black currant added. Surprisingly, the addition of black currant made the cat's claw/oolong tea extract much more water soluble. It also made the composition of cat's claw/oolong tea extract with the addition of black currant taste much more better (more sweet, less bitter and less astringent to the taste).

Figure 15:
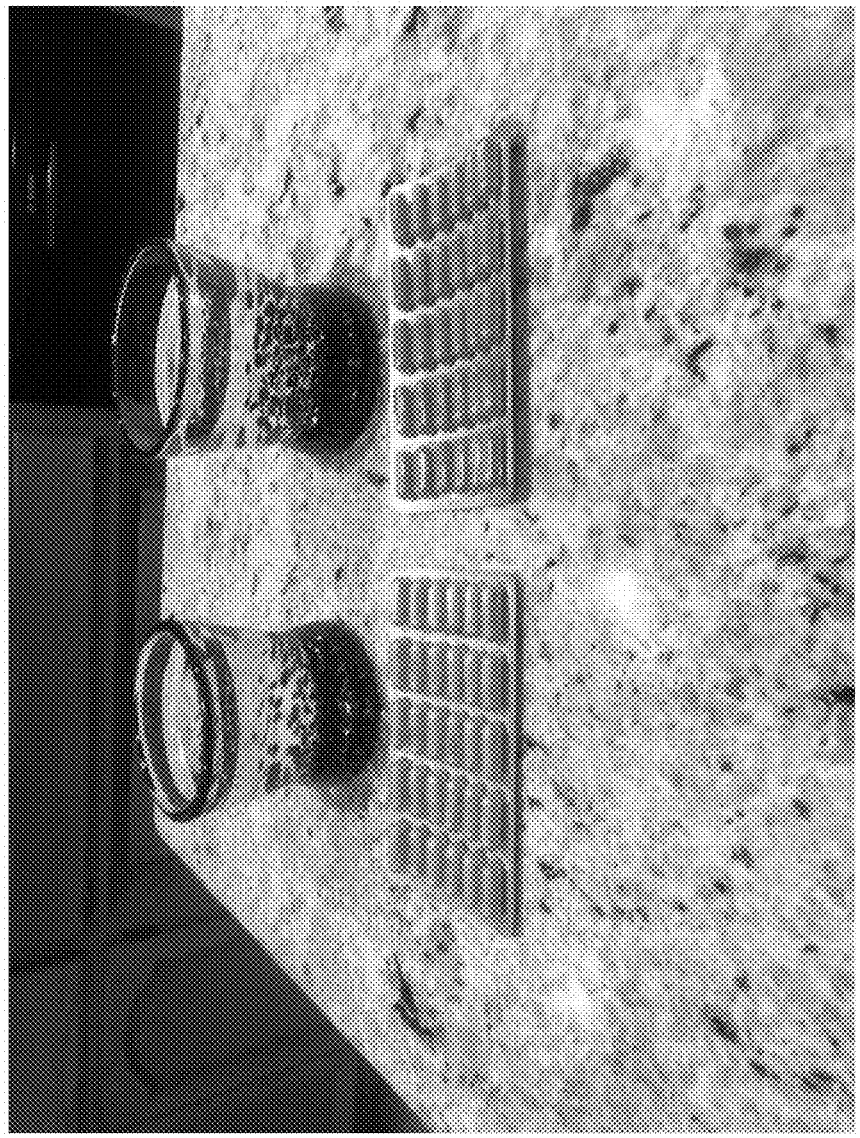
FIG. 15 shows cat's claw/oolong tea extract in capsules compared to cat's claw/oolong tea/black currant capsules.

FIG. 15 shows capsules of cat's claw/oolong tea extract in front of a glass of water (left side of figure). On the right side are capsules with the same cat's claw/oolong tea extract with 50 mg of Euro black currant extract added.

Figure 16:
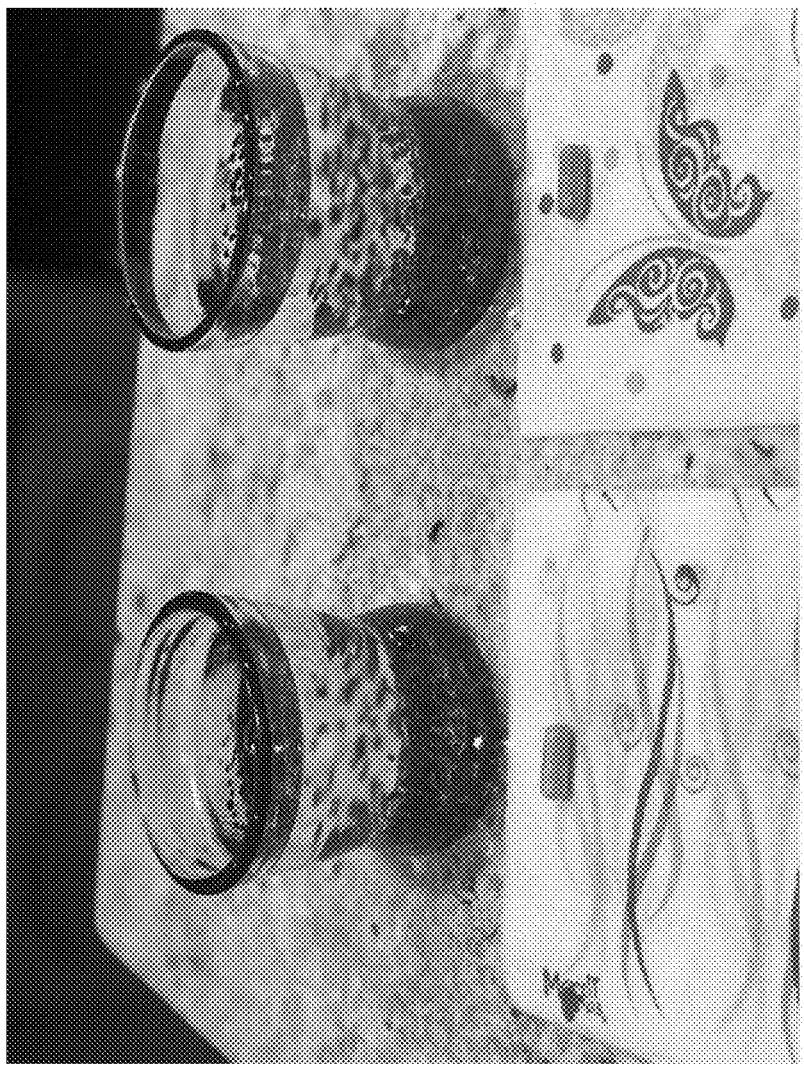
FIG. 16 shows a glass of water with a cat's claw/oolong tea extract containing capsule versus a cat's claw/oolong tea/black currant containing capsule.

FIG. 16 shows a single capsule in front of a glass of water. Left side is the cat's claw/oolong tea extract versus the right side that contains the cat's claw/oolong tea extract/black currant combination.

Figure 17A:
FIGS. 17A, 17B, and 17C compare initial dissolution (within 5 seconds) in water of a cat's claw/oolong tea single capsule versus a cat's claw/oolong tea/black currant capsule.
Figure 17B:
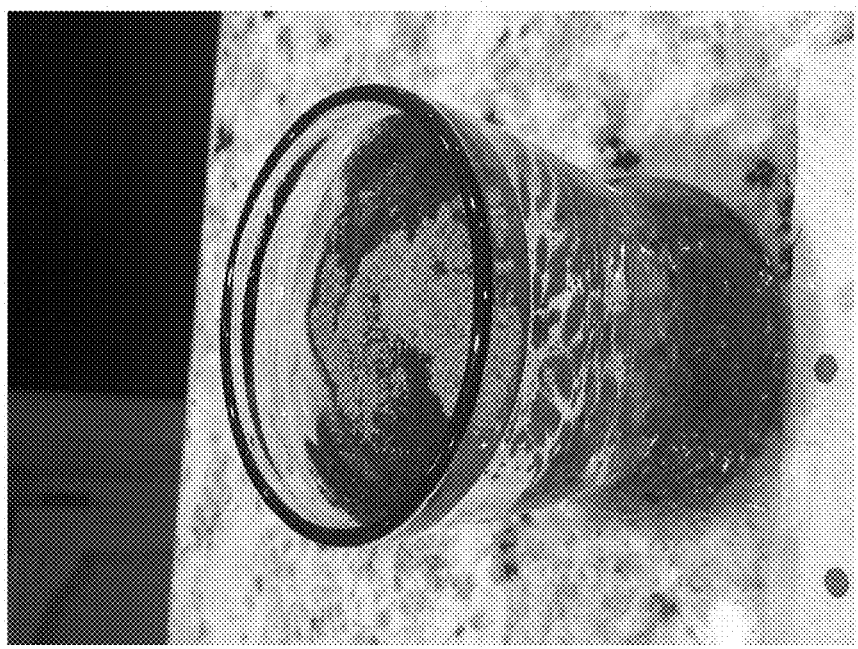
Figure 17C:
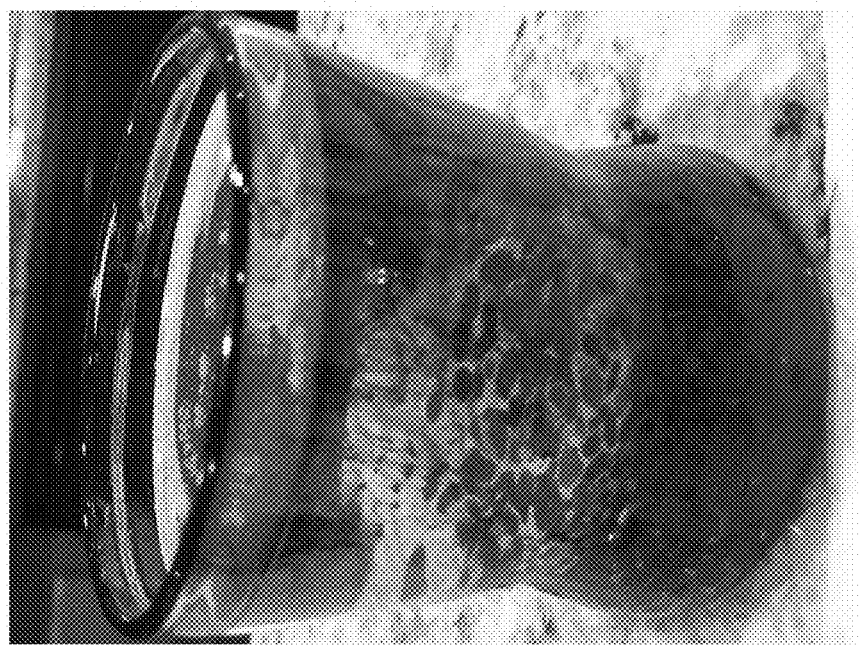

FIG. 17A shows clumping (within 5 seconds) and water insolubility of the cat claw/oolong tea extract combination. FIG. 17B demonstrates the clumping (within 5 seconds) of the cat's claw/oolong tea/black currant combination. FIG. 17C demonstrates that within 10 seconds, surprisingly, the cat's claw/oolong tea/black currant combination begins to self-dissolve in water.

Figure 18A:
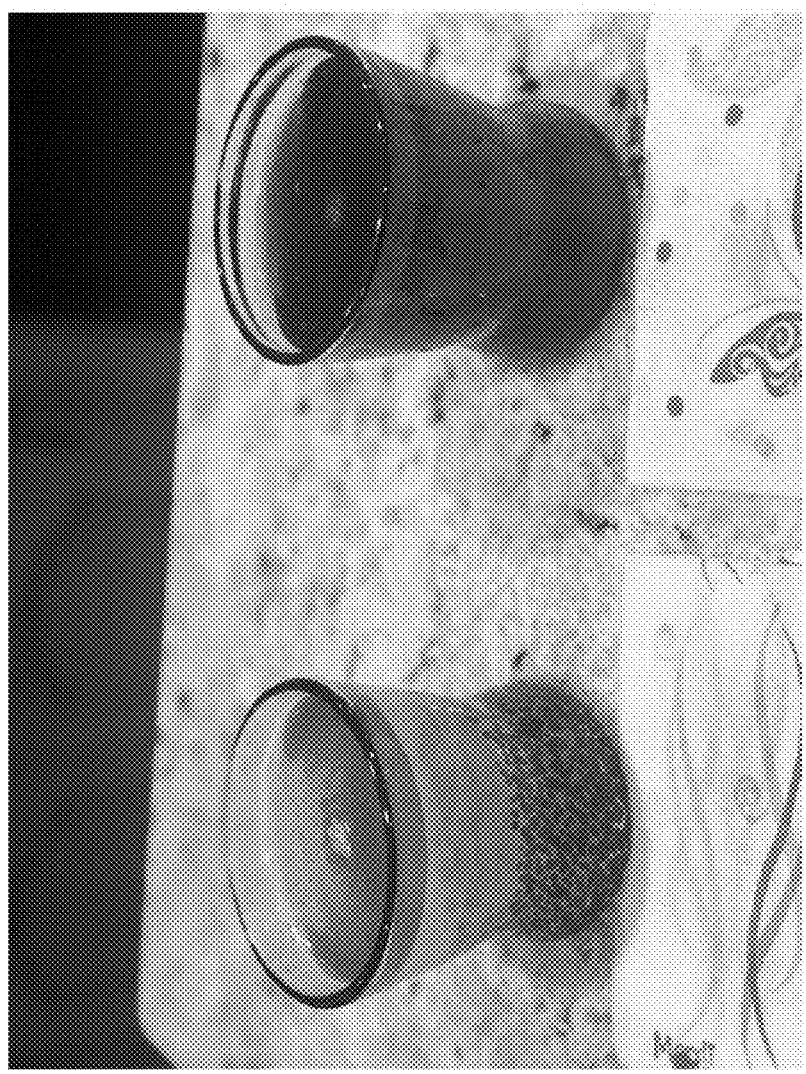
FIGS. 18A, 18B, and 18C compares dissolution in water of a cat's claw/oolong tea extract compared to a cat's claw/oolong tea extract with black currant.
Figure 18B:
Figure 18C:

FIG. 18A demonstrates following stirring with a spoon that the cat's claw/oolong tea extract (left side) remains insoluble with a clump of insoluble material at the top of the glass of water; whereas the addition of black currant (right side) which makes the water turn dark purple also makes the mixture much more water soluble with little to no clumps of material at the top of the glass. FIG. 18B is a close up of the cat's claw/oolong tea extract showing water-insolubility with a large clump on insoluble material at top of glass of water after stirring. FIG. 18C is a close up of the cat's claw/oolong tea/black currant combination demonstrating near dissolution in water following stirring. The addition of black currant also makes the solution taste much sweeter (less bitter and less astringent tasting).

Example 8: In Vivo Testing for Improvement of Cognition and Memory

Further in vivo studies are used to test the any one of the compositions described herein for its effectiveness in the reduction of brain "plaque and tangle" load and improvement of cognition and memory. 40-60 men and women are selected for a clinical study. Subjects have age-associated memory impairment (AAMI), and expecting to have worsening symptoms of memory loss within the 6-month study period, but are in good general health otherwise.

This study includes a placebo group, i.e. the subjects are divided into two groups, one of which receives the test composition, which is any one of the compositions described herein formulated as capsules (such as two 375 mg or 670 mg capsules containing Composition A with a meal; preferably lunch), and the other receives a placebo (two capsules containing capsules without the study product active ingredients). The subjects are benchmarked as to memory, cognition, focus, concentration, reasoning and other symptoms associated with mild-cognitive impairment (MCI). Subjects in the test groups receive a therapeutic dose of the combination study product extract or placebo for 6 months, with analysis for short-term memory, cognition, focus and concentration to be examined at 0, 1, 3, and 6-months of treatment. Accurate records with regards to memory, focus and concentration are kept as to the benchmarked symptoms in both groups and at the end of the study these results are compared. The results also are compared between members of each group. In addition, the results for each subject are compared to the symptoms reported by each subject before the study began. Activity of the test composition used is illustrated by the attenuation of the typical cognitive decline, decline in short-term memory, cognition, focus and concentration, and/or associated behavioral disruptions associated with age-associated memory impairment (AAMI). It is expected that Composition A, which is combination of black currant extract, oolong tea extract, and cat's claw extract, will reduce brain "plaque and tangle" load and/or improve cognition and memory.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

What is claimed is:

1. A pill, tablet, caplet, soft gelatin capsule, hard gelatin capsule, lozenge, sachet bag, emulsion, tea bag, suppository, or sterile packaged powder consisting essentially of a mixture of a black currant extract, an *Uncaria tomentosa* extract, and an oolong tea extract, wherein the water solubility of the mixture is increased relative to the water solubility of a pill, tablet, caplet, soft gelatin capsule, hard gelatin capsule, lozenge, sachet bag, emulsion, tea bag, suppository, or sterile packaged powder consisting essentially of *Uncaria tomentosa* extract, oolong tea extract, and no black currant extract.

2. The pill, tablet, caplet, soft gelatin capsule, hard gelatin capsule, lozenge, sachet bag, emulsion, tea bag, suppository, or sterile packaged powder of claim 1, wherein the black currant extract "consists essentially of from about 10% to about 35% w/w proanthocyanidins, anthocyanidins, anthocyanins, or a combination thereof.

3. The pill, tablet, caplet, soft gelatin capsule, hard gelatin capsule, lozenge, sachet bag, emulsion, tea bag, suppository, or sterile packaged powder of claim 2, wherein the black currant extract "consists essentially of about 25% w/w proanthocyanidins, anthocyanidins, anthocyanins, or a combination thereof.

4. The pill, tablet, caplet, soft gelatin capsule, hard gelatin capsule, lozenge, sachet bag, emulsion, tea bag, suppository, or sterile packaged powder of claim 1, wherein the mixture consists essentially of from about 10 mg to about 100 mg of black currant extract.

5. The pill, tablet, caplet, soft gelatin capsule, hard gelatin capsule, lozenge, sachet bag, emulsion, tea bag, suppository, or sterile packaged powder of claim 1, wherein the mixture consists essentially of from about 1% to about 10% w/w black currant extract.

6. The pill, tablet, caplet, soft gelatin capsule, hard gelatin capsule, lozenge, sachet bag, emulsion, tea bag, suppository, or sterile packaged powder of claim 1, wherein the mixture consists essentially of from about 100 mg to about 500 mg of *Uncaria tomentosa* extract.

7. The pill, tablet, caplet, soft gelatin capsule, hard gelatin capsule, lozenge, sachet bag, emulsion, tea bag, suppository, or sterile packaged powder of claim 1, wherein the mixture consists essentially of from about 10% to about 40% w/w *Uncaria tomentosa* extract.

8. The pill, tablet, caplet, soft gelatin capsule, hard gelatin capsule, lozenge, sachet bag, emulsion, tea bag, suppository, or sterile packaged powder of claim 1, wherein the mixture consists essentially of from about 100 mg to about 500 mg of oolong tea extract.

9. The pill, tablet, caplet, soft gelatin capsule, hard gelatin capsule, lozenge, sachet bag, emulsion, tea bag, suppository, or sterile packaged powder of claim 1, wherein the mixture consists essentially of from about 10% to about 40% w/w of oolong tea extract.

10. The soft gelatin capsule or hard gelatin capsule of claim 1, which has a weight from about 200 mg to about 1000 mg.

\* \* \* \* \*